(12) United States Patent
Musbach et al.

(10) Patent No.: US 8,292,827 B2
(45) Date of Patent: Oct. 23, 2012

(54) MICROMACHINED MEDICAL DEVICES

(75) Inventors: Frank A. Musbach, Pleasanton, CA (US); Tracee E. J. Eidenschink, Wayzata, MN (US); Richard C. Gunderson, Maple Grove, MN (US); Richard J. Olson, Blaine, MN (US); Daniel K. Tomaschko, Save, MN (US); Richard L. Goodin, Blaine, MN (US); Todd H. Turnlund, Park City, UT (US); Jason Todd Lenz, Maplewood, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1155 days.

(21) Appl. No.: 11/301,195

(22) Filed: Dec. 12, 2005

(65) Prior Publication Data

US 2007/0135763 A1 Jun. 14, 2007

(51) Int. Cl.
*A61B 5/00* (2006.01)
(52) U.S. Cl. .......................................... 600/585
(58) Field of Classification Search .................. 604/523, 604/264, 525, 528; 600/585
See application file for complete search history.

(56) References Cited

U.S. PATENT DOCUMENTS

| | | | |
|---|---|---|---|
| 4,547,193 A | 10/1985 | Rydell | |
| 4,580,551 A | 4/1986 | Siegmund et al. | |
| 4,753,238 A | 6/1988 | Gaiser | |
| 4,795,439 A | 1/1989 | Guest | |
| 4,998,923 A | 3/1991 | Samson et al. | |
| 5,095,915 A | 3/1992 | Engelson | |
| 5,106,455 A | 4/1992 | Jacobsen et al. | |
| 5,228,441 A | 7/1993 | Lundquist | |
| 5,238,004 A | 8/1993 | Sahatjian et al. | |
| 5,315,996 A | 5/1994 | Lundquist | |
| 5,322,064 A | 6/1994 | Lundquist | |
| 5,328,472 A | 7/1994 | Steinke et al. | |
| 5,329,923 A | 7/1994 | Lundquist | |
| 5,334,145 A | 8/1994 | Lundquist et al. | |
| 5,372,144 A | 12/1994 | Mortier et al. | |
| 5,437,288 A | 8/1995 | Schwartz et al. | |
| 5,477,856 A | 12/1995 | Lundquist | |
| 5,507,751 A | 4/1996 | Goode et al. | |
| 5,507,766 A | 4/1996 | Kugo et al. | |
| 5,569,197 A | 10/1996 | Helmus et al. | |
| 5,573,520 A | 11/1996 | Schwartz et al. | |
| 5,695,506 A | 12/1997 | Pike et al. | |
| 5,741,429 A | 4/1998 | Donadio, III et al. | |
| 5,743,876 A * | 4/1998 | Swanson .................... | 604/96.01 |
| 5,772,609 A | 6/1998 | Nguyen et al. | |
| 5,772,669 A | 6/1998 | Vrba | |
| 5,788,707 A | 8/1998 | Del Toro et al. | |
| 5,797,856 A | 8/1998 | Frisbie et al. | |

(Continued)

FOREIGN PATENT DOCUMENTS

EP 0608853 A2 8/1994

(Continued)

*Primary Examiner* — Nicholas Lucchesi
*Assistant Examiner* — Diva K Chander
(74) *Attorney, Agent, or Firm* — Seager, Tufte & Wickhem LLC

(57) ABSTRACT

Medical devices that include micromachined hypotubes or that have themselves been micromachined can provide advantages in flexibility, strength and other desirable properties. Examples of such medical devices may include catheters such as guide catheters and balloon catheters. Such devices may also include dual shaft medical devices in which an outer shaft is reversibly lockable onto an inner shaft.

16 Claims, 28 Drawing Sheets

U.S. PATENT DOCUMENTS

| | | |
|---|---|---|
| 5,833,632 A | 11/1998 | Jacobsen et al. |
| 5,902,290 A | 5/1999 | Peacock, III et al. |
| 5,968,069 A | 10/1999 | Dusbabek et al. |
| 6,001,068 A | 12/1999 | Uchino et al. |
| 6,004,279 A | 12/1999 | Crowley et al. |
| 6,014,919 A | 1/2000 | Jacobsen et al. |
| 6,017,319 A | 1/2000 | Jacobsen et al. |
| 6,048,339 A | 4/2000 | Zirps et al. |
| 6,068,635 A | 5/2000 | Gianotti |
| 6,077,295 A | 6/2000 | Limon et al. |
| 6,096,045 A | 8/2000 | Del Toro et al. |
| 6,102,932 A | 8/2000 | Kurz |
| 6,123,712 A | 9/2000 | DiCaprio et al. |
| 6,139,510 A | 10/2000 | Palermo |
| 6,168,617 B1 | 1/2001 | Blaeser et al. |
| 6,174,327 B1 | 1/2001 | Mertens et al. |
| 6,203,558 B1 | 3/2001 | Dusbabek et al. |
| 6,241,758 B1 | 6/2001 | Cox |
| 6,245,098 B1 | 6/2001 | Feeser et al. |
| 6,260,458 B1 | 7/2001 | Jacobsen et al. |
| 6,287,291 B1 | 9/2001 | Bigus et al. |
| 6,287,315 B1 | 9/2001 | Wijeratne et al. |
| 6,302,893 B1 | 10/2001 | Limon et al. |
| 6,325,814 B1 | 12/2001 | Euteneuer et al. |
| 6,342,066 B1 | 1/2002 | Toro et al. |
| 6,371,962 B1 | 4/2002 | Ellis et al. |
| 6,398,802 B1 | 6/2002 | Yee |
| 6,428,489 B1 | 8/2002 | Jacobsen et al. |
| 6,428,566 B1 | 8/2002 | Holt |
| 6,431,039 B1 | 8/2002 | Jacobsen et al. |
| 6,436,090 B1 | 8/2002 | Sanchez et al. |
| 6,440,088 B1 | 8/2002 | Jacobsen et al. |
| 6,508,803 B1 | 1/2003 | Horikawa et al. |
| 6,514,280 B1 | 2/2003 | Gilson |
| 6,517,569 B2 | 2/2003 | Mikus et al. |
| 6,530,947 B1 | 3/2003 | Euteneuer et al. |
| 6,533,805 B1 | 3/2003 | Jervis |
| 6,562,064 B1 | 5/2003 | deBeer |
| 6,576,008 B2 | 6/2003 | Devonec et al. |
| 6,579,246 B2 | 6/2003 | Jacobsen et al. |
| 6,592,549 B2 | 7/2003 | Gerdts et al. |
| 6,592,568 B2 | 7/2003 | Campbell |
| 6,592,569 B2 | 7/2003 | Bigus et al. |
| 6,602,280 B2 | 8/2003 | Chobotov |
| 6,607,555 B2 | 8/2003 | Patterson et al. |
| 6,610,046 B1 | 8/2003 | Usami et al. |
| 6,623,491 B2 | 9/2003 | Thompson |
| 6,629,981 B2 | 10/2003 | Bui et al. |
| 6,652,508 B2 | 11/2003 | Griffin et al. |
| 6,660,031 B2 | 12/2003 | Tran et al. |
| 6,669,716 B1 | 12/2003 | Gilson et al. |
| 6,676,666 B2 | 1/2004 | Vrba et al. |
| 6,699,274 B2 | 3/2004 | Stinson |
| 6,702,802 B1 | 3/2004 | Hancock et al. |
| 6,712,827 B2 | 3/2004 | Ellis et al. |
| 6,723,071 B2 | 4/2004 | Gerdts et al. |
| 6,726,714 B2 | 4/2004 | DiCaprio et al. |
| 6,743,210 B2 | 6/2004 | Hart et al. |
| 6,766,720 B1 | 7/2004 | Jacobsen et al. |
| 6,773,446 B1 | 8/2004 | Dwyer et al. |
| 6,802,849 B2 | 10/2004 | Blaeser et al. |
| 6,918,882 B2 | 7/2005 | Skujins et al. |
| 7,001,369 B2 | 2/2006 | Griffin et al. |
| 7,074,197 B2 | 7/2006 | Reynolds et al. |
| 2003/0009208 A1 | 1/2003 | Snyder et al. |
| 2003/0069522 A1 | 4/2003 | Jacobsen et al. |
| 2003/0093059 A1 | 5/2003 | Griffin et al. |
| 2003/0125709 A1 | 7/2003 | Eidenschink |
| 2004/0111044 A1 | 6/2004 | Davis et al. |
| 2004/0167437 A1 | 8/2004 | Sharrow et al. |
| 2004/0167441 A1 | 8/2004 | Reynolds et al. |
| 2004/0181174 A2* | 9/2004 | Davis et al. ............... 600/585 |
| 2005/0065456 A1 | 3/2005 | Eskuri |
| 2005/0187602 A1 | 8/2005 | Eidenschink |
| 2005/0209582 A1* | 9/2005 | Quinn et al. ............... 604/528 |
| 2005/0234499 A1 | 10/2005 | Olson et al. |
| 2006/0189896 A1 | 8/2006 | Davis et al. |
| 2007/0083132 A1 | 4/2007 | Sharrow |
| 2007/0135763 A1 | 6/2007 | Musbach |

FOREIGN PATENT DOCUMENTS

| | | |
|---|---|---|
| EP | 0 778 039 A1 | 6/1997 |
| EP | 0937481 A1 | 8/1999 |
| EP | 1457224 A1 | 9/2004 |
| EP | 1 144 039 B1 | 12/2005 |
| JP | 8-257128 A | 10/1996 |
| JP | 2003-175110 A | 6/2003 |
| JP | 2004-275767 A | 10/2004 |
| WO | 95/24236 A1 | 9/1995 |
| WO | 97/44086 A1 | 11/1997 |
| WO | 9810694 | 3/1998 |
| WO | 0025849 | 5/2000 |
| WO | 03/004086 A2 | 1/2003 |

\* cited by examiner

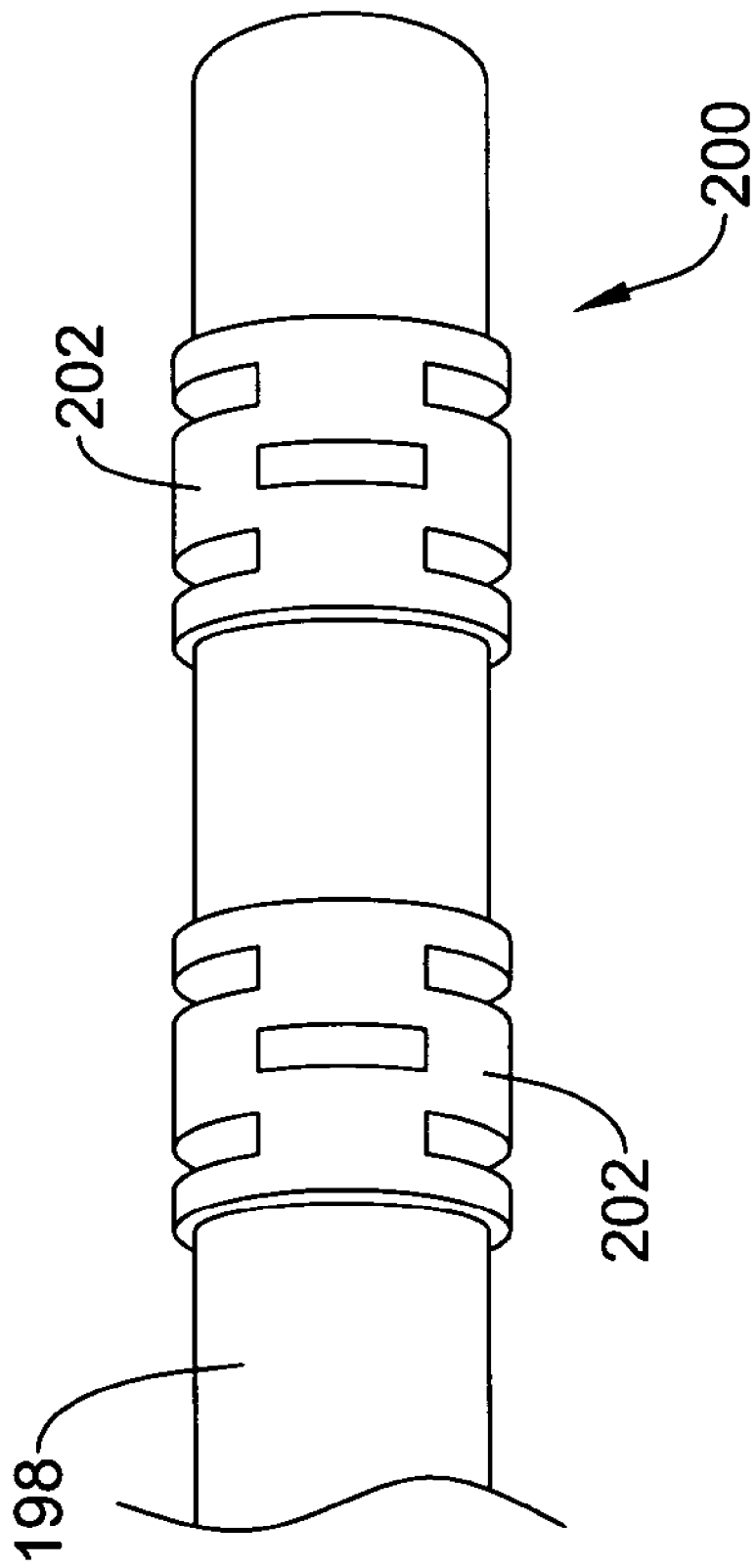

MICROMACHINED MEDICAL DEVICES

TECHNICAL FIELD

The invention relates generally to medical devices and more specifically to medical devices that include micromachined components. Such medical devices may include, for example, catheters.

BACKGROUND

Medical devices such as catheters may be subject to a number of often conflicting performance requirements such as flexibility, strength, minimized exterior diameter, maximized interior diameter, and the like. In particular, oftentimes there is a balance between a need for flexibility and a need for strength. Therefore, a need remains for improved medical devices such as catheters that are configured for an optimal balance between flexibility, strength, and other desired properties.

SUMMARY

The invention pertains to improved medical devices providing advantages in flexibility, strength and other desired properties.

Accordingly, an example embodiment of the invention can be found in a catheter that includes an elongate tube extending from a distal region of the catheter to a proximal region of the catheter. A number of slots extending radially about the elongate tube are disposed along the elongate tube. A polymeric dual-lumen liner is disposed within the elongate tube.

Another example embodiment of the invention can be found in a catheter that includes an elongate metal tube extending from a distal region of the catheter to a proximal region of the catheter. A number of flexibility-induced slots extending radially about the elongate metal tube are disposed along the elongate metal tube. A polymeric sleeve is disposed about the elongate metal tube while a polymeric dual-lumen liner is disposed within the elongate metal tube.

Another example embodiment of the invention can be found in a catheter having a distal region defining a distal end and a proximal region defining a proximal end. The catheter includes a polymer sheath that extends from the distal end of the catheter to the proximal end of the catheter. A micromachined hypotube is disposed over the polymer sheath and includes a distal region defining a distal end and a proximal region defining a proximal end. The micromachined hypotube extends from the distal region of the catheter to the proximal region of the catheter such that the polymer sheath extends distally from the distal end of the micromachined hypotube. The micromachined hypotube includes a number of radially-extending, flexibility-inducing slots disposed along the micromachined hypotube.

Another example embodiment of the invention can be found in a catheter that includes an elongate shaft and at least one micromachined marker band that is disposed within a distal region of the catheter.

Another example embodiment of the invention can be found in a catheter that includes an elongate polymer sheath, the polymer sheath defining a lumen extending through the polymer sheath. A balloon is secured to the elongate polymer sheath within a distal region of the elongate polymer sheath. At least one micromachined compression ring is disposed proximal of the balloon within the elongate polymer sheath lumen.

Another example embodiment of the invention can be found in a catheter that includes an inner shaft defining a guidewire lumen and an inflation lumen and an outer shaft disposed over the inner shaft such that the outer shaft extends distally beyond a distal end of the inner shaft. A balloon defining a balloon interior is disposed on the outer shaft within a distal region of the catheter. A micromachined hypotube is disposed within the guidewire lumen and extends distally through the balloon interior. The micromachined hypotube includes one or more cutouts to accommodate one or more marker bands disposed on the micromachined hypotube.

Another example embodiment of the invention can be found in a balloon catheter that includes an elongate shaft and a balloon disposed on the elongate shaft. The balloon includes a proximal waist bonded to the elongate shaft and a distal waist bonded to the elongate shaft. The distal waist and the proximal waist each include a number of radially disposed cuts intended to improve flexibility.

Another example embodiment of the invention can be found in a medical device that includes an outer shaft and an inner shaft disposed within the outer shaft such that the inner shaft extends beyond an outer shaft end of the outer shaft. A collapsible cage is disposed over the inner shaft. The collapsible shaft includes a first end that is attached to the outer shaft end and a second end that is attached to an attachment point on the inner shaft. The collapsible cage is moveable between a moveable position in which the outer shaft may move with respect to the inner shaft and a locked position in which the outer shaft is locked to the inner shaft and cannot move.

Another example embodiment of the invention can be found in a medical device that includes an outer shaft and an inner shaft disposed within the outer shaft such that the inner shaft extends beyond an outer shaft end of the outer shaft. A polymer sleeve is disposed over the inner shaft. The polymer sleeve includes a first end that is attached to the outer shaft end and a second end that is attached to an attachment point on the inner shaft. The polymer sleeve is moveable between a rotation position in which the outer shaft may rotate with respect to the inner shaft and a locked position in which the outer shaft is locked to the inner shaft and cannot rotate.

Another example embodiment of the invention can be found in a medical device that includes a micromachined hypotube having a number of radially-extending, flexibility-inducing slots disposed along the micromachined hypotube. A polymer insert is disposed within a lumen defined by the micromachined hypotube. The polymer insert has a non-round radial cross-section and includes at least one lumen disposed within the polymer insert.

Another example embodiment of the invention can be found in a catheter that includes an elongate hypotube having a hypotube lumen. The elongate hypotube extends from a distal region of the catheter to a proximal region of the catheter and includes a number of slots disposed within the elongate hypotube. An inflatable balloon is disposed about a distal region of the elongate hypotube. An outer sheath is disposed proximal to the inflatable balloon covering at least the distal region of the elongate hypotube such that the outer sheath seals the plurality of slots so that the hypotube lumen may be used for inflating and deflating the inflatable balloon.

Another example embodiment of the invention can be found in a micromachined hypotube that includes a first number of slots that are disposed within a first portion of the micromachined hypotube and a second number of slots that are disposed within a second portion of the micromachined hypotube. The slots extend at least partially circumferentially around the micromachined hypotube. The second number of slots include adjacent slots having a spacing therebetween that is less than a spacing between adjacent slots within the first plurality of slots.

Another example embodiment of the invention can be found in a micromachined hypotube having a number of slots disposed within the micromachined hypotube. The slots extend from the outer surface to the inner surface and each of the number of slots include a first portion extending at an acute angle with respect to the axial axis and a second portion arranged at least substantially perpendicular to the first portion.

Another example embodiment of the invention can be found in a micromachined hypotube that has an inner surface, an outer surface and a number of radially-extending slots disposed on the micromachined hypotube, each of the radially-extending slots having a first diameter at the inner surface and a second diameter at the outer surface, the second diameter being greater than the first diameter.

Another example embodiment of the invention can be found in a micromachined hypotube that has an axial axis. A number of slots are disposed at least substantially perpendicular to the axial axis. At least some of the slots have a first edge and a second edge, the first edge of at least some of the slots including a button that extends toward the second edge of at least some of the slots.

The above summary of the present invention is not intended to describe each disclosed embodiment or every implementation of the present invention. The Figures, Detailed Description and Examples which follow more particularly exemplify these embodiments.

BRIEF DESCRIPTION OF THE FIGURES

The invention may be more completely understood in consideration of the following detailed description of various embodiments of the invention in connection with the accompanying drawings, in which:

FIG. 19 is a view of a portion of a catheter in accordance with an embodiment of the invention;

Figure 1:
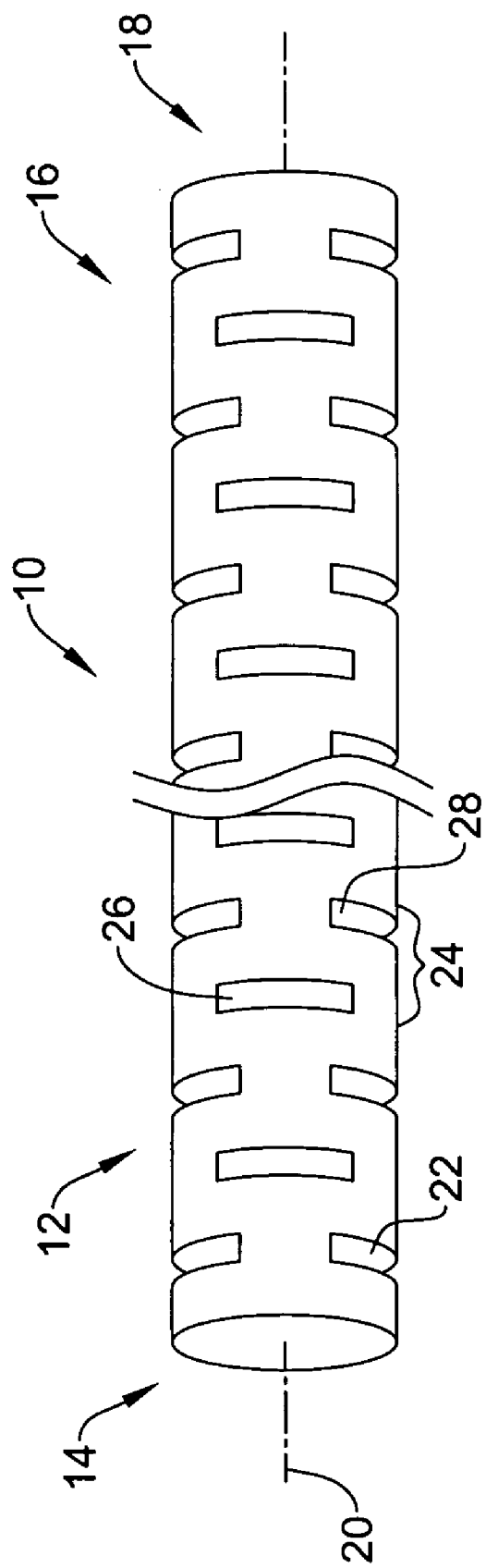
FIG. 1 is a view of a micromachined hypotube in accordance with an embodiment of the invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following description should be read with reference to the drawings wherein like reference numerals indicate like elements throughout the several views. The drawings, which are not necessarily to scale, depict illustrative embodiments of the claimed invention.

The invention pertains generally to medical devices that include micromachined hypotubes or other elements that have been micromachined. A variety of micromachined hypotubes are within the scope of the invention and are useful in the medical devices described herein. FIGS. 1-5 illustrate particular, but non-limiting, micromachined hypotubes as contemplated within the boundaries of the invention.

FIG. 1 illustrates a micromachined hypotube 10 having a proximal region 12 defining a proximal end 14 and a distal region 16 defining a distal end 18. The micromachined hypotube 10 can be seen as having an axial axis 20 extending the length of the hypotube 10. One or more slots 22 are disposed along the length of the micromachined hypotube 10. In the illustrated embodiment, the slots 22 are arranged at least substantially perpendicular to the axial axis 20. In other instances, the slots 22 may be arranged at an angle with respect to the axial axis 20, or may even be parallel to the axial axis 20.

Each of the slots 22 extend only partially around the circumference of the micromachined hypotube 10. In some instances, an individual slot 22 may extend about half way around the circumference of the micromachined hypotube. In other cases, an individual slot 22 can extend more than halfway around, if for example, increased flexibility is of highest importance. Conversely, if it is desired to provide additional column strength, perhaps with a certain sacrifice in flexibility, it is contemplated that each individual slot 22 may extend less than halfway around the micromachined hypotube 10.

If an individual slot 22 extends only a relatively short circumferential difference about the micromachined hypotube 10, it is contemplated that two, three or more slots 22 may be disposed radially about a single axial position along the micromachined hypotube 10. In some instances, an individual slot 22 may extend completely through the micromachined hypotube. In some cases, one or more of the individual slots 22 may have a depth less than a wall thickness of the micromachined hypotube 10.

It can be seen that individual slots 22 may be considered as being in pairs 24, with a pair 24 including a first slot 26 and a second slot 28. In some embodiments, as illustrated, the first slot 26 can have a first radial position on the micromachined hypotube 10 while the second slot 28 occupies a second radial position that is rotated from the first radial position. In some embodiments, as illustrated, the second slot 28 can be rotated about 90 degrees from the first slot 26. In other instances, the radial rotation can vary, especially if, for example, first slot 26 and first slot 28 are either longer or shorter than the illustrated length.

In some instances, and as illustrated, an individual slot 22 may be rectangular in shape. In some instances, an individual slot 22 may be curved, such as a semi-circular shape. In some cases, an individual slot 22 may be diamond-shaped. An individual slot 22 may be formed using any suitable technique, such as saw cutting, a laser, or even by electrical discharge machining (EDM). Additional suitable techniques include chemical etching and abrasive grinding.

The micromachined hypotube 10 may be formed of any suitable polymeric or metallic material. In some cases, the micromachined hypotube 10 may be formed of a suitably stiff polymer such as carbon fibers, liquid crystal polymers, polyimide, and the like. In some instances, the micromachined hypotube 10 may be formed of a metallic material such as stainless steel or a nickel-titanium alloy such as Nitinol or other metallic or polymeric shape-memory material. The micromachined hypotube 10 may include a combination of metal tubes and polymer tubes, if desired.

The micromachined hypotube 10 may be formed having any desired length, width, material thickness, and slot size as required to satisfy the requirements of any particular application. Additional details concerning micromachined hypotube 10, including the manufacture thereof, can be found, for example, in U.S. Pat. No. 6,766,720 and published U.S. Patent Application No. 2004/0181174A2, each of which are fully incorporated, in their entirety, by reference herein.

Figure 2:
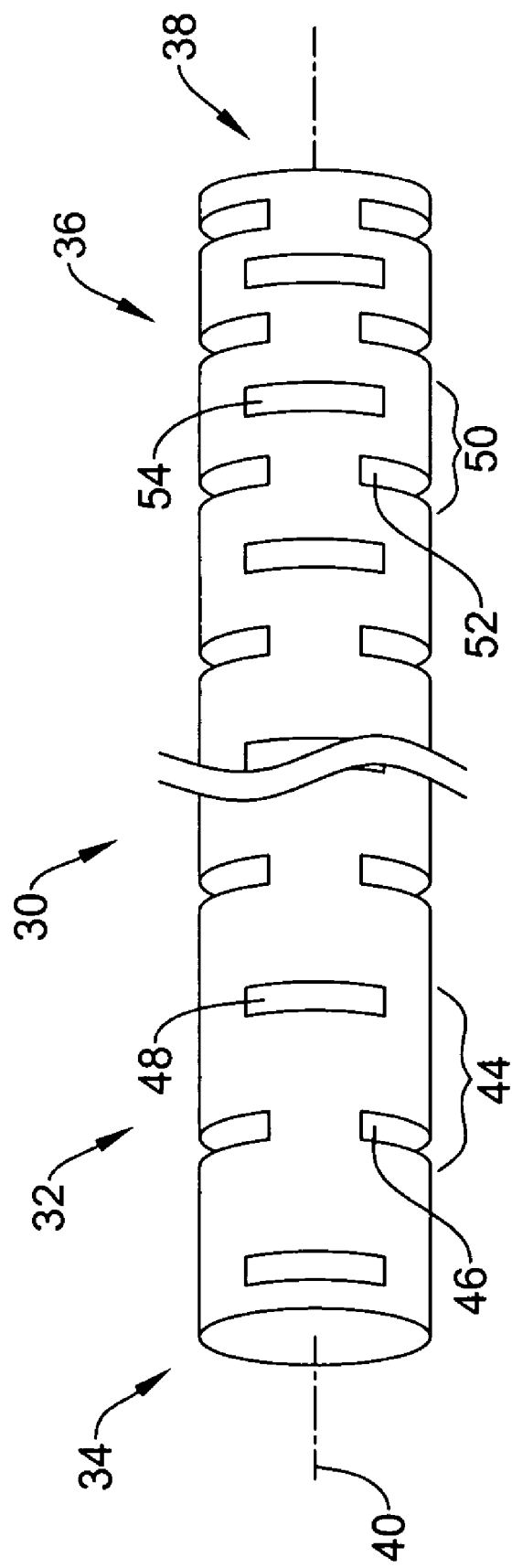
FIG. 2 is a view of a micromachined hypotube in accordance with an embodiment of the invention.

In FIG. 1, each of the slots 22 disposed within micromachined hypotube 10 are evenly axially spaced. FIG. 2 illustrates an embodiment in which the inter-slot spacing is varied.

In particular, FIG. 2 shows a micromachined hypotube 30 having a proximal region 32 defining a proximal end 34 and a distal region 36 defining a distal end 38. The micromachined hypotube 30 has an axial axis 40 extending the length of the hypotube 30. A number of slots 42 are disposed along the length of the micromachined hypotube 10. In the illustrated embodiment, the slots 42 are arranged at least substantially perpendicular to the axial axis 40. In other instances, the slots 42 may be arranged at an angle with respect to the axial axis 40.

Each of the slots 42 extend only partially around the circumference of the micromachined hypotube 30. In some instances, an individual slot 42 may extend about half way around the circumference of the micromachined hypotube. In other cases, an individual slot 42 can either extend less than halfway around, or conversely, more than halfway around, depending on the relative importance of flexibility and strength. As discussed with respect to FIG. 1, individual slots 42 can be radially offset from adjacent slots 42.

As noted, FIG. 2 illustrates variety in inter-slot spacing. In the proximal region 32, for example, individual slots 42 may be considered as being in pairs 44, with a pair 44 including a first slot 46 and a second slot 48. Similarly, in the distal region 36, individual slots may be considered as being in pairs 50, with a pair 50 including a first slot 52 and a second slot 54. It can be seen in FIG. 2 that the axial spacing between first slot 46 and second slot 48 of pair 44 is greater than the axial spacing between first slot 52 and second slot 54 of pair 50. This can be done to provide relatively greater flexibility within the distal region 36.

In some instances, the inter-slot spacing within the proximal region 32 may be a first constant while the inter-slot spacing within the distal region 36 may be a second, smaller constant. In some cases, the inter-slot spacing may change on a step-wise fashion moving from the proximal region 32 to the distal region 36. In some instances, the inter-slot spacing may change in a more continuous manner when moving from the proximal region 32 to the distal region 36.

Figure 3:
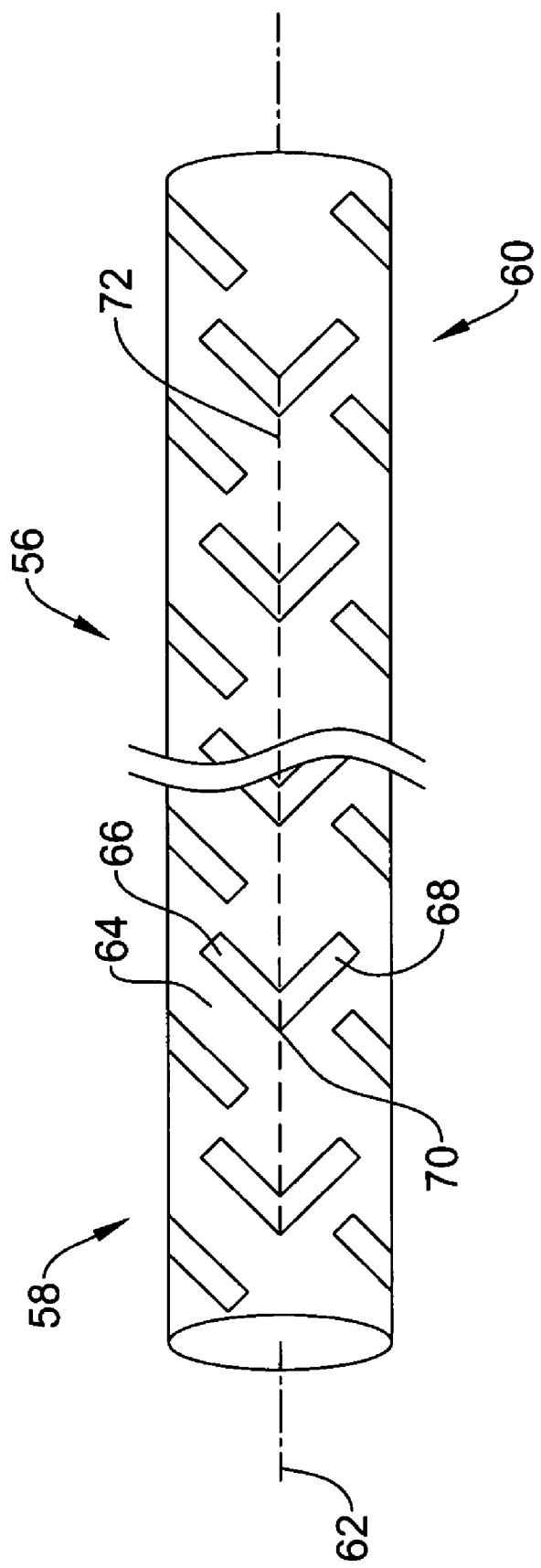
FIG. 3 is a view of a micromachined hypotube in accordance with an embodiment of the invention.

FIG. 3 illustrates another exemplary slot pattern. In particular, FIG. 3 shows a micromachined hypotube 56 having a proximal region 58 and a distal region 60. An axial axis 62 extends through the micromachined hypotube 56. The micromachined hypotube 56 includes a number of slots 64. Each slot 64 can be seen to include a first portion 66, a second portion 68 and an intervening apex 70. In some instances, as illustrated, the apex 70 of several axially aligned slots 64 may be seen to lie along a line 72 that is parallel with the axial axis 62.

It can be seen that the first portion 66 forms an acute angle with the line 72, while the second portion 68 is at least substantially perpendicular to the first portion 66. In some instances, the first portion 66 and the second portion 68 may form similar angles with the line 72 yet form an angle of less than about 90 degrees between the first portion 66 and the second portion 68. In other instances, the first portion 66 and the second portion 68 may form an angle between themselves that is greater than about 90 degrees. As discussed previously with respect to FIGS. 1 and 2, adjacent slots 64 may be radially offset.

Figure 4:
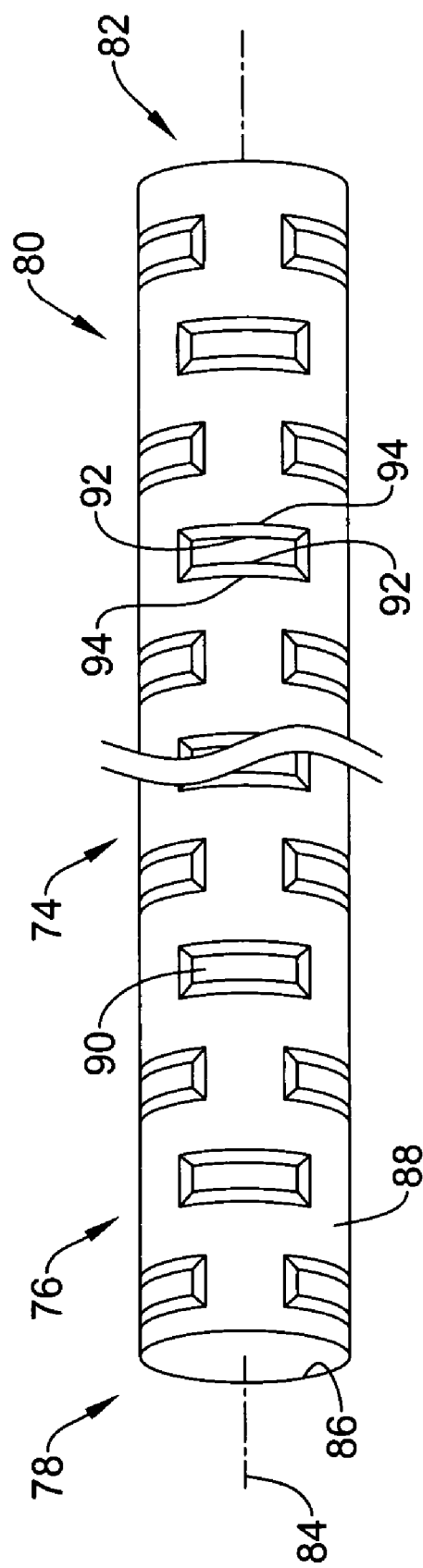
FIG. 4 is a view of a micromachined hypotube in accordance with an embodiment of the invention.

FIG. 4 illustrates a micromachined hypotube 74 that has a distal region 76 defining a distal end 78 and a proximal region 80 defining a proximal end 82. The micromachined hypotube defines an axial axis 84 extending therethrough. The micromachined hypotube 74 has an inner surface 86 and an outer surface 88. A number of tapered slots 90 are disposed within the micromachined hypotube 74 and are at least substantially radially aligned, i.e. are at least substantially perpendicular to the axial axis 84. As discussed previously with respect to FIGS. 1 and 2, adjacent tapered slots 90 may be radially offset.

The tapered slots 90 can be seen to have opposing lower edges 92 at inner surface 86 and opposing upper edges 94 at outer surface 88. The tapered slots 90 are constructed such that each tapered slot 90 has a major dimension that is at least substantially perpendicular to the axial axis 84 and a minor dimension that is orthogonal to the major dimension. In some instances, the major dimension may be considered to be a length of the tapered slot 90, while the minor dimension may be considered to be a width of the tapered slot. In some instances, as illustrated, each tapered slot 90 has a minor dimension, or width between opposing upper edges 94, at the outer surface 88 that is larger than the minor dimension, or width between opposing lower edges 92, of the same tapered slot 90 at the inner surface 86. In some cases, the width of the tapered slot 90 at the outer surface 88 can be about twice the corresponding inner surface 86 width.

As a result of tapered slots 90 having a relatively wider opening at the outer surface 88, relatively greater flexibility can be obtained in micromachined hypotube 74 as the micromachined hypotube 74 can bend further before opposing upper edges 94 come into contact with each other. As a result of providing tapered slots 90 with a relatively narrower opening at the inner surface 86, relatively greater column strength may be obtained in micromachined hypotube 74 as the bottom edges of the tapered slot 90 will contact each other as compressive force is applied to the micromachined hypotube 74. By varying the relative distance between opposing lower edges 92 and the corresponding opposing upper edges 94, a balance between flexibility and strength may be optimized for any particular application.

In some instances, as illustrated, the ends of each tapered slot 90 may be similarly tapered. In other cases, the slot ends may not be tapered. Each of the tapered slots 90 extend only partially around the circumference of the micromachined hypotube 74. In some instances, an individual tapered slot 90 may extend about half way around the circumference of the micromachined hypotube 74. In other cases, an individual tapered slot 90 can either extend less than halfway around, or conversely, more than halfway around, depending on the relative importance of flexibility and strength. As discussed with respect to FIG. 1, individual tapered slots 90 can be radially offset from adjacent tapered slots 90.

Figure 5:
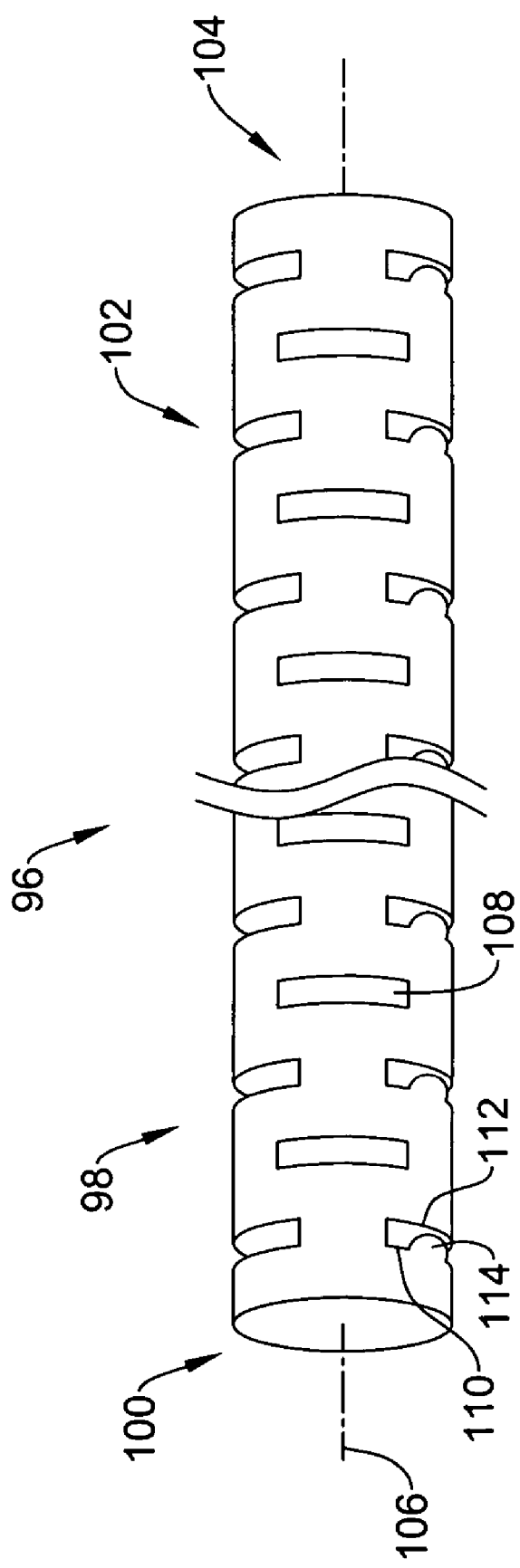
FIG. 5 is a view of a micromachined hypotube in accordance with an embodiment of the invention.

FIG. 5 shows a micromachined hypotube 96 having a proximal region 98 defining a proximal end 100 and a distal region 102 defining a distal region 104. An axial axis 106 extends through the micromachined hypotube 96. A number of slots 108 are disposed within the micromachined hypotube 96 and are at least substantially radially aligned, i.e. are at least substantially perpendicular to the axial axis 106. As discussed previously with respect to FIGS. 1 and 2, adjacent slots 108 may be radially offset.

Each of the slots 108 can be seen as including a proximal edge 110 and a distal edge 112. Some of the slots 108 may include a protrusion or button 114 on at least one of the proximal edge 110 and the distal edge 112. These buttons 114 may be integrally formed with micromachined hypotube 96. In some instances, the buttons 114 can be added subsequently to forming the micromachined hypotube 96. In such cases, it is contemplated that buttons 114 could include or be formed from small amounts of molten material such as solder, or perhaps the stainless steel or even nitinol from which the micromachined hypotube 96 was formed. In some instances, the buttons 114 may be formed via electrical discharge machining (EDM).

In some instances, as illustrated, the buttons 114 may be provided or formed along proximal edge 110 of the slots 108. In other cases, buttons 114 could be included along the distal edge 112 of the slots 108. It is contemplated that buttons 114 could be provided along the proximal edge 110 of some of the slots 108 and along the distal edge 112 of some of the other slots 108. The number and placement of the buttons 114 can be varied to achieve a desired level of column support.

Figure 6:
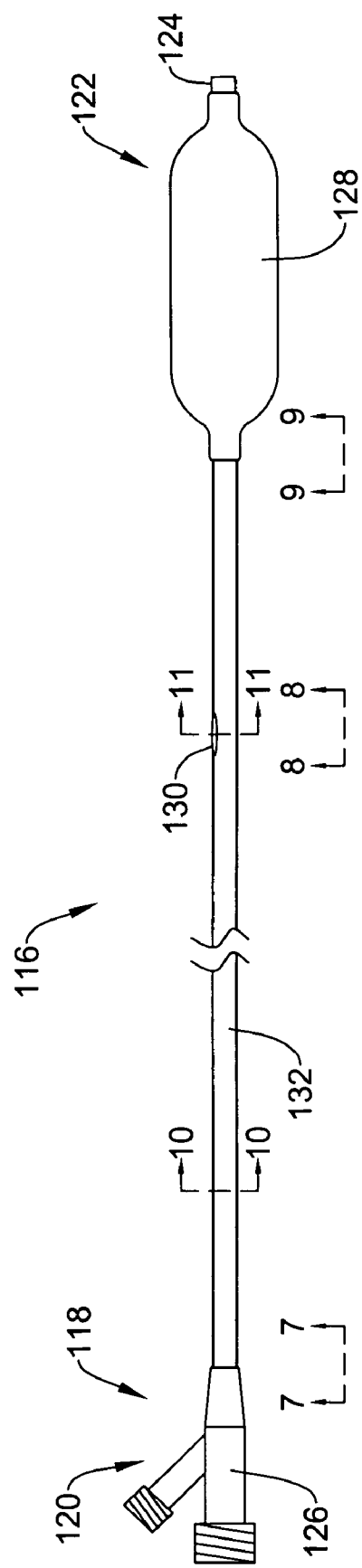
FIG. 6 is a view of a catheter in accordance with an embodiment of the invention.

FIGS. 6 through 11 illustrate an example use of the micromachined hypotubes 10, 30, 56, 74 and 96 discussed herein. FIG. 6 shows a catheter 116 having a proximal region 118 defining a proximal end 120 and a distal region 122 defining a distal end 124. Catheter 116 can be one of a variety of different catheters, but is preferably an intravascular catheter. Examples of intravascular catheters include balloon catheters, atherectomy catheters, stent delivery catheters such as those adapted to deploy self-expanding stents, filter delivery catheters, diagnostic catheters and guide catheters. As illustrated, FIG. 6 portrays a balloon catheter, but the invention is not limited to such. A hub 126 is secured to the catheter 116 near the proximal end 120. A balloon 128 is secured to the catheter 116 within the distal region 124. The hub 126 and the balloon 128 can be of any known construction.

In the illustrated embodiment, a guidewire port 130 is disposed within the catheter 116 at a position proximal of the balloon 128 but well distal of the hub 126. The guidewire port 130 can be positioned relatively close to the distal end 124 of the catheter 116 to provide catheter 116 with rapid exchange capabilities, even if a guidewire lumen (not illustrated in this view) extends throughout the length of the catheter 116.

In some embodiments, the catheter 116 includes an elongate shaft 132 extending from the hub 126 to at least the distal region 122, if not the distal end 124, of the catheter 116. The elongate shaft 132 may be of any suitable material. In some instances, the elongate shaft 132 may be a micromachined hypotube such as those described with respect to FIGS. 1-5. The slots are not shown in FIG. 6, simply for clarity. As will be discussed with respect to FIGS. 9 and 10, the catheter 116 may include one more polymeric elements within an interior of the elongate shaft 132.

Figure 7:
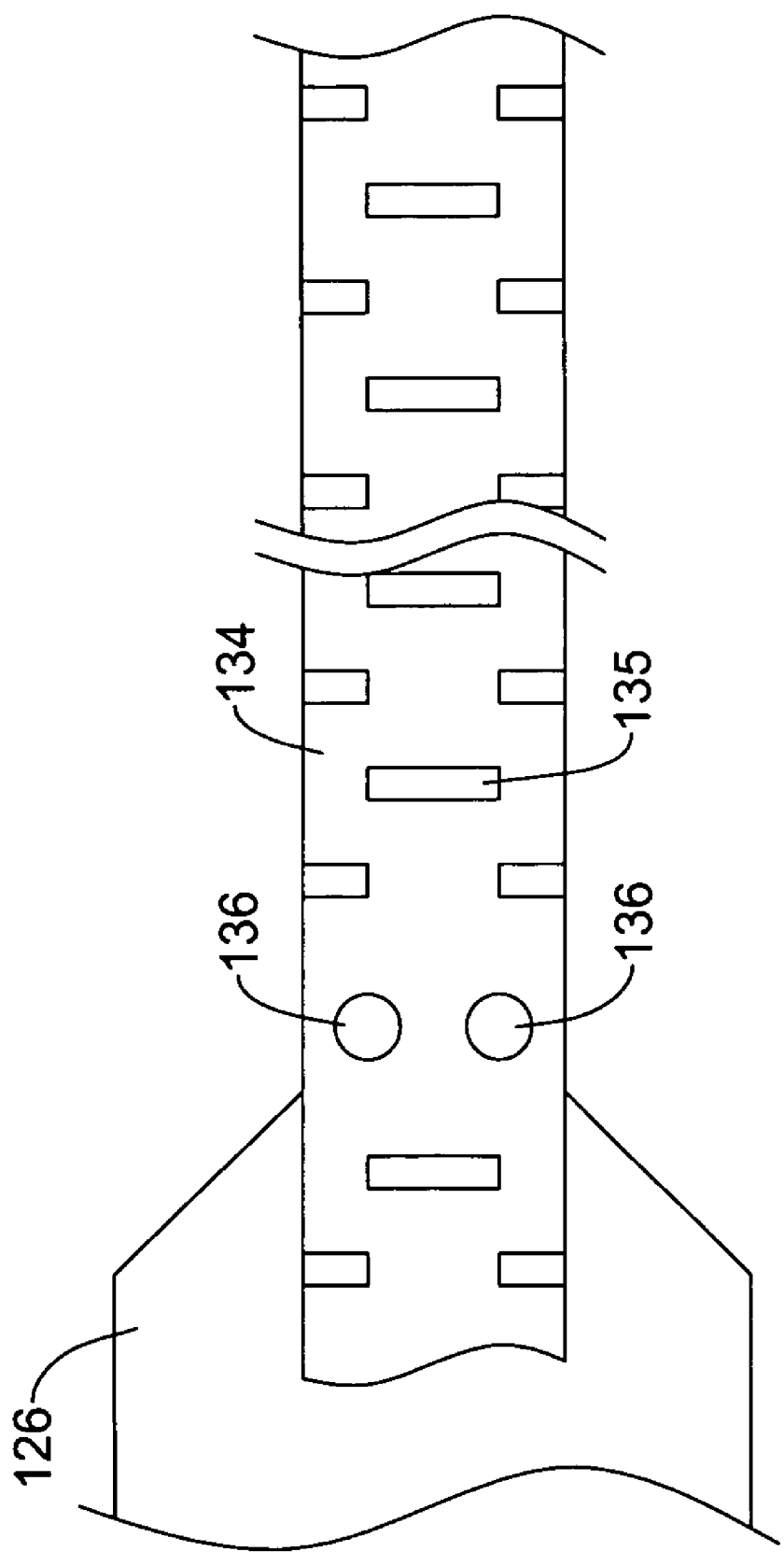
FIG. 7 is a partial longitudinal cross-sectional view of a proximal portion of the catheter of FIG. 6.

FIG. 7 is a partial cross-sectional view of a portion of the proximal region 118, including a portion of hub 126. A micromachined hypotube 134 can be seen as extending distally out of the hub 126. Similar to several of the micromachined hypotubes discussed previously, micromachined hypotube 134 includes a number of radially-oriented slots 135. While slots 135 are shown as being similar to those shown in FIG. 1, it should be recognized that a number of other arrangements are contemplated.

The micromachined hypotube 134 also includes several apertures 136. One or more apertures 136 may be spaced about the circumference of the micromachined hypotube 134. In some embodiments, a total of four apertures 136 may be equally spaced about the circumference of the micromachined hypotube 134. In other instances, either fewer than four or perhaps even more than four apertures 136 may be included. While the illustrated apertures 136 are round, other shapes are contemplated.

The apertures 136 are included within the micromachined hypotube 134 in order to provide for additional attachment points between the micromachined hypotube 134 and the polymeric liner (which will be discussed in greater detail hereinafter) positioned within the micromachined hypotube 134. In some instances, additional polymeric material may be melted into the apertures 136 to secure the polymeric liner to the micromachined hypotube 134.

Figure 8:
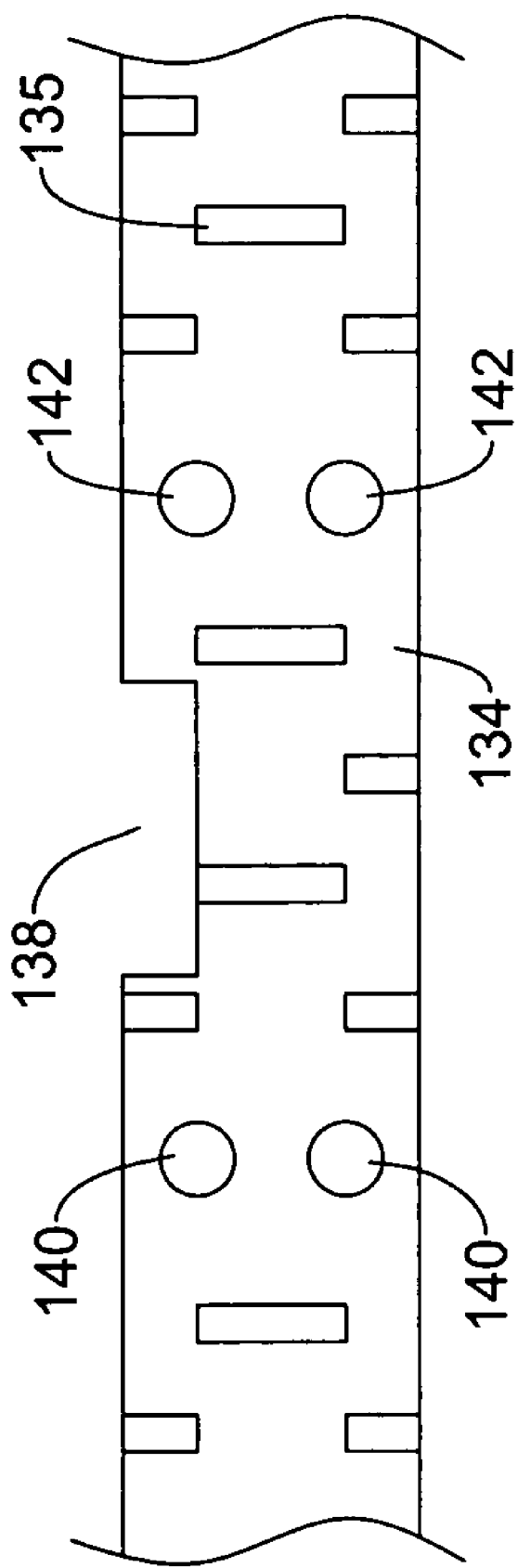
FIG. 8 is a partial longitudinal cross-sectional view of an intermediate portion of the catheter of FIG. 6.

FIG. 8 shows another section of the micromachined hypotube 134, corresponding to either side of the guidewire port 130 (FIG. 7). This portion of the micromachined hypotube 134 includes a guidewire aperture 138 that is configured and positioned to align with the guidewire port 130 and thus permit access to the interior of the micromachined hypotube 134. It should be recognized that the guidewire aperture 138 may be somewhat generalized in FIG. 8, and may have a curved or semicircular shape, depending on how it is formed. One or more apertures 140 can be positioned just proximal of the guidewire aperture 138 and one or more apertures 142 can be positioned just distal of the guidewire aperture 138.

The apertures 140 and 142 may be spaced about the circumference of the micromachined hypotube 134. In some embodiments, a total of four apertures 140 and a total of four apertures 142 may be equally spaced about the circumference of the micromachined hypotube 134. In other instances, either fewer than four or perhaps even more than four of apertures 140 and 142 may be included. While the illustrated apertures 140 and 142 are round, other shapes are contemplated.

The apertures 140 and 142 are included within the micromachined hypotube 134 in order to provide for additional attachment points between the micromachined hypotube 134 and the polymeric liner positioned therein. In some instances, additional polymeric material may be melted into the apertures 140 and 142 to secure the polymeric liner to the micromachined hypotube 134.

Figure 9:
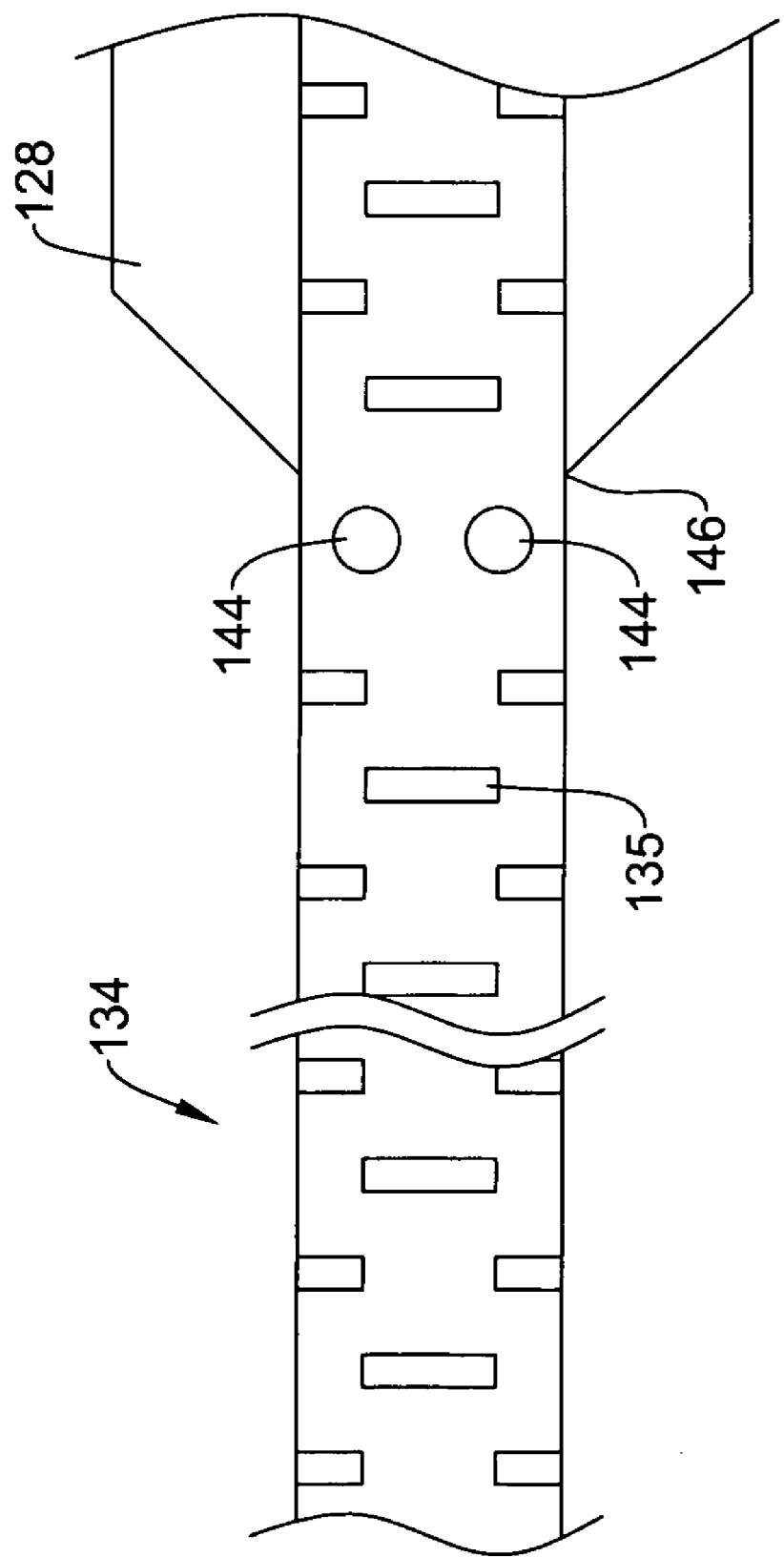
FIG. 9 is a partial longitudinal cross-sectional view of a distal portion of the catheter of FIG. 6.

FIG. 9 is a partial cross-section view of a portion of the distal region 122, showing the micromachined hypotube 134 as well as a portion of the balloon 128. One or more apertures 144 can be positioned just proximal of a proximal end 146 of the balloon 128. The apertures 144 may be spaced about the circumference of the micromachined hypotube 134. In some embodiments, a total of four apertures 144 may be equally spaced about the circumference of the micromachined hypotube 134. In other instances, either fewer than four or perhaps even more than four of apertures 144 may be included. While the illustrated apertures 144 are round, other shapes are contemplated.

The apertures 144 are included within the micromachined hypotube 134 in order to provide for additional attachment points between the micromachined hypotube 134 and the polymeric liner positioned therein. In some instances, additional polymeric material may be melted into the apertures 144 to secure the polymeric liner to the micromachined hypotube 134.

Figure 10:
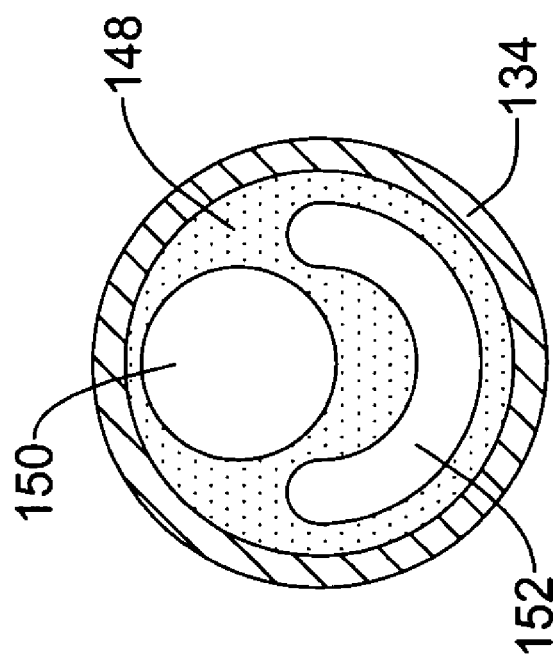
FIG. 10 is a cross-sectional view taken along line 10-10 of FIG. 6.

FIG. 10 is a cross-section of FIG. 6, taken along line 10-10, illustrating the construction of the elongate shaft 132 (FIG. 6). A polymeric liner 148 can be seen positioned within micromachined hypotube 134. In the illustrated embodiment, the polymeric liner 148 includes a guidewire lumen 150 and an inflation lumen 152. In some instances, the polymeric liner 148 could include either a greater or lesser number of lumens, as dictated by the intended use of catheter 116 (FIG. 6).

The polymeric liner 148 can be made of any suitable polymeric material. Examples of suitable materials include polyethylene, polyurethane, elastomeric polyamides, block polyamide/ethers (such as PEBAX®), silicones, co-polymers, thermoplastic polymers such as a co-polyester thermoplastic elastomer such as that available commercially under the ARNITEL® name, and fluoropolymers such as PTFE. In particular embodiments, the polymeric liner 148 may be formed of high density polyethylene. If the polymeric liner 148 is formed of high density polyethylene, the same material may be used to melt into apertures 136 (FIG. 7), apertures 140 and 142 (FIG. 8) and apertures 144 (FIG. 9), in order to secure polymeric liner 148 to micromachined hypotube 134.

Figure 11:
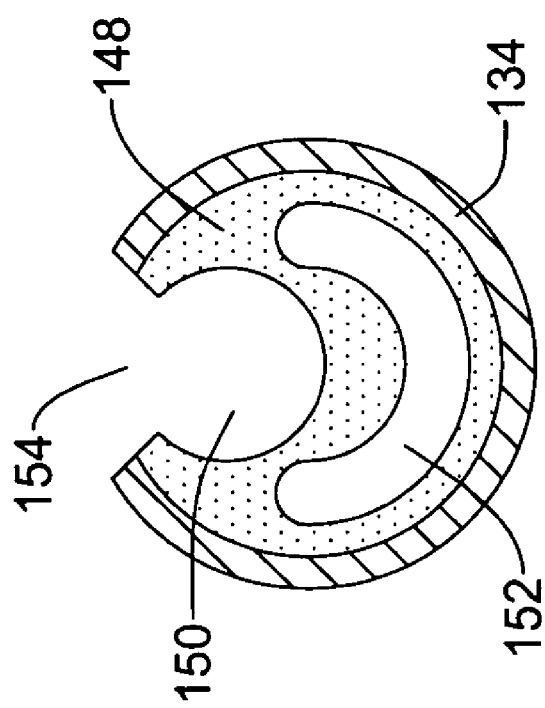
FIG. 11 is a cross-sectional view taken along line 11-11 of FIG. 6.

FIG. 11 is a cross-section of FIG. 6, taken along line 11-11, illustrating additional construction details of the elongate shaft 132 (FIG. 6) as pertaining to the guidewire port (136). In FIG. 11, the micromachined hypotube 134 and the polymeric liner 148 have been milled, ground, or otherwise processed or provide an opening 154 that permits access to the guidewire lumen 150 from a position exterior to the catheter 116.

Figure 12:
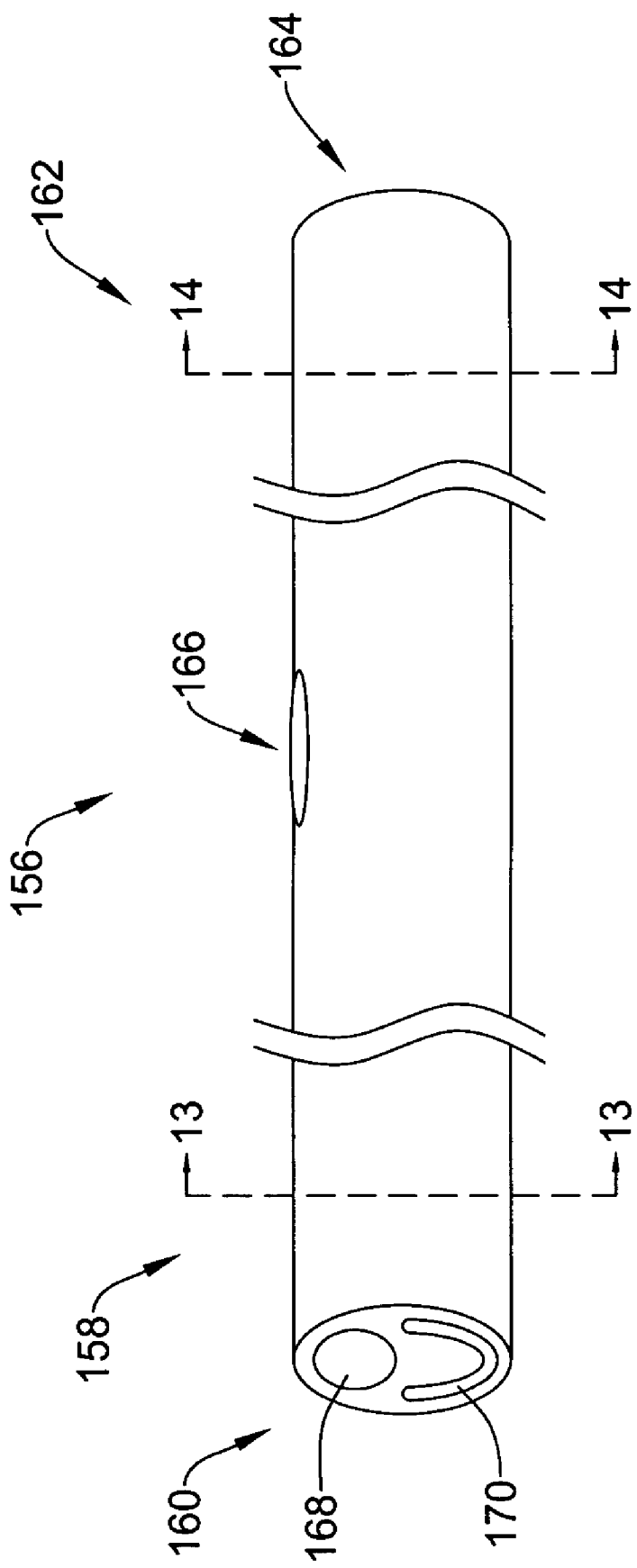
FIG. 12 is a view of a catheter in accordance with an embodiment of the invention.

FIGS. 12-15 illustrate another example use of the micromachined hypotubes 10, 30, 56, 74 and 96 discussed herein. FIG. 12 shows a catheter 156 having a proximal region 158 defining a proximal end 160 and a distal region 162 defining a distal end 164. Catheter 156 can be one of a variety of different catheters, but is preferably an intravascular catheter. Examples of intravascular catheters include balloon catheters, atherectomy catheters, stent delivery catheters, filter delivery catheters, diagnostic catheters and guide catheters.

Catheter 156 can include one or more constructional elements, as will be discussed. As illustrated, the catheter 156 includes a guidewire lumen 168 and an inflation lumen 170, although in some instances catheter 156 can include additional lumens. In some cases, catheter 156 may only include a single lumen that can be used both as a guidewire lumen and as an inflation lumen, should catheter 156 be a balloon catheter. For clarity, a balloon is not illustrated in FIG. 12. The catheter 156 also includes a guidewire port 166 that provides access to the interior of the guidewire lumen 168.

Figure 14:
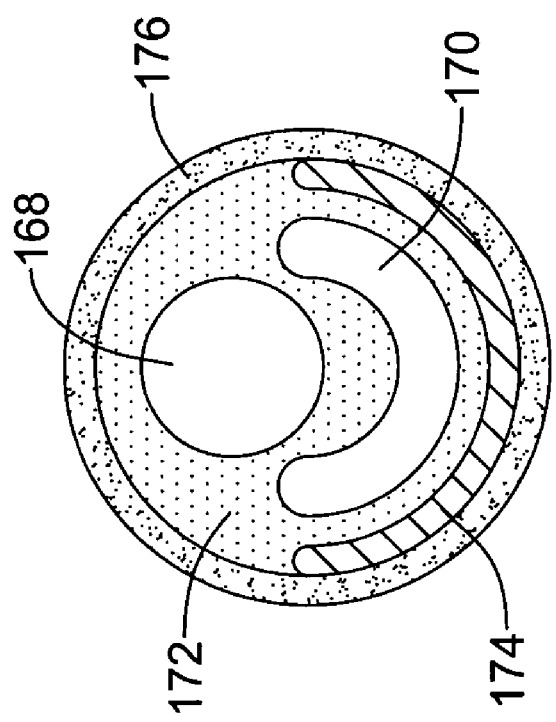
FIG. 14 is a cross-sectional view taken along line 14-14 of FIG. 12.
Figure 13:
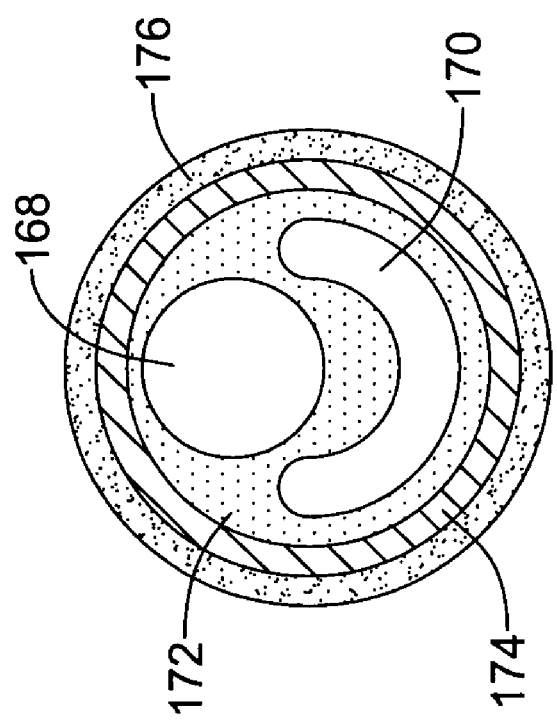
FIG. 13 is a cross-sectional view taken along line 13-13 of FIG. 12.

FIGS. 13 and 14 are cross-sections taken through FIG. 12. FIG. 13 is taken through the proximal region 158 of FIG. 12 while FIG. 14 is taken through the distal region 162 of FIG. 12. As shown in FIG. 13, the catheter 156 can be seen to include an inner polymeric liner 172 that defines guidewire lumen 168 and inflation lumen 170, an outer polymeric sheath 176 and an intervening micromachined hypotube 174. The micromachined hypotube 174 can include any construction discussed herein with respect to position, configuration and frequency of slots.

In FIG. 14, which is a cross-section taken distally of the guidewire port 166 (FIG. 12), it can be seen that only a portion of the micromachined hypotube 174 remains. In particular, the upper portion, which would otherwise interfere with a guidewire (not illustrated) gaining access to the guidewire lumen 168, has been removed.

Figure 15:
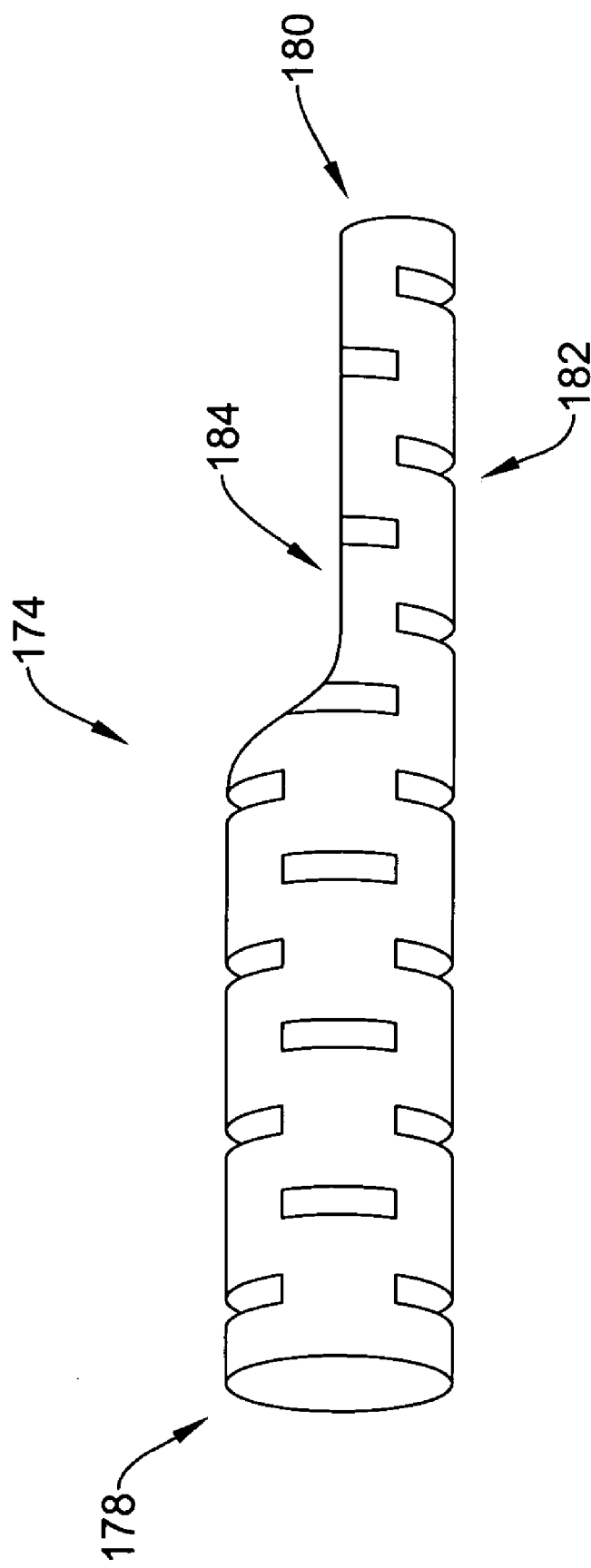
FIG. 15 is a partial longitudinal view of structure present within the catheter of FIG. 12.

FIG. 15 is a side view of the micromachined hypotube 174, which has a proximal end 178, a distal region 180 and a distal end 182. It can be seen that much of the material has been removed in the distal region 180, forming profile 184. In some instances, the material can be removed from the distal region 180 using any suitable technique such as grinding, cutting, laser and the like. In some cases, it is contemplated that profile 184 can instead be formed by crushing the distal region 180 of the micromachined hypotube 174, rather than material removal. This may necessitate, however, drilling or otherwise forming an aperture through the crushed portion to permit a guidewire (not shown) to pass from the interior of the micromachined hypotube 174 to the exterior of the micromachined hypotube 174 as the guidewire passes into the profile 184.

Figure 16:
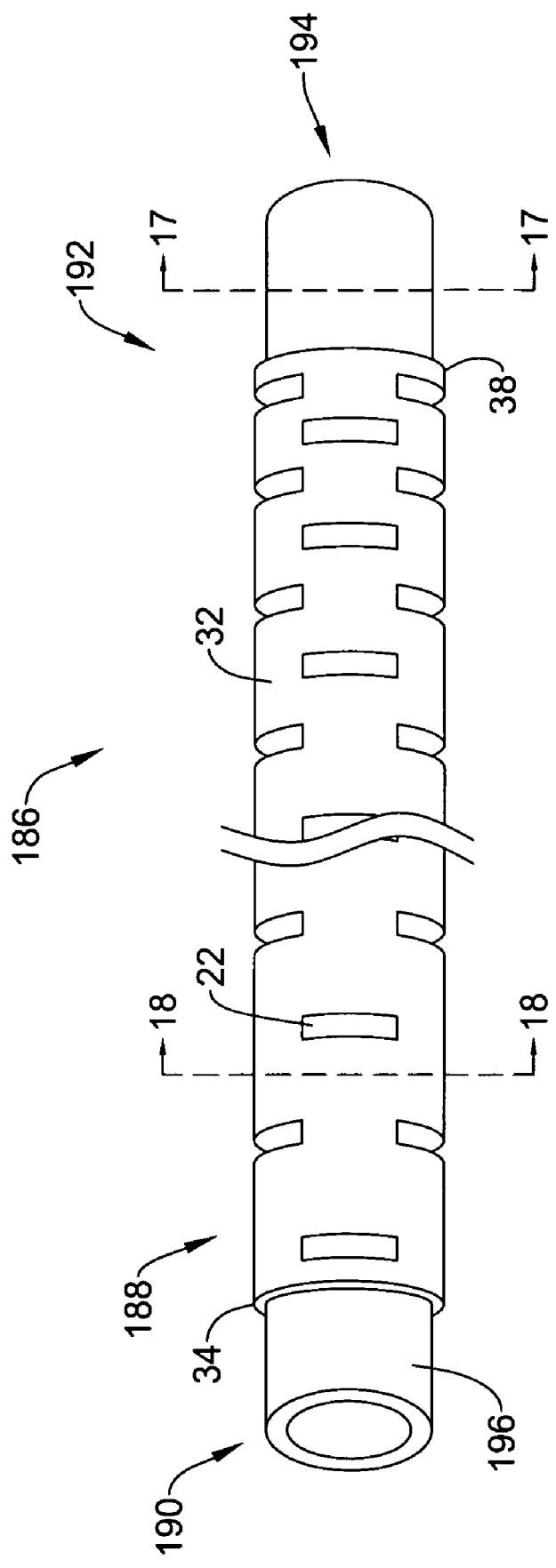
FIG. 16 is a view of a catheter in accordance with an embodiment of the invention.
Figure 18:
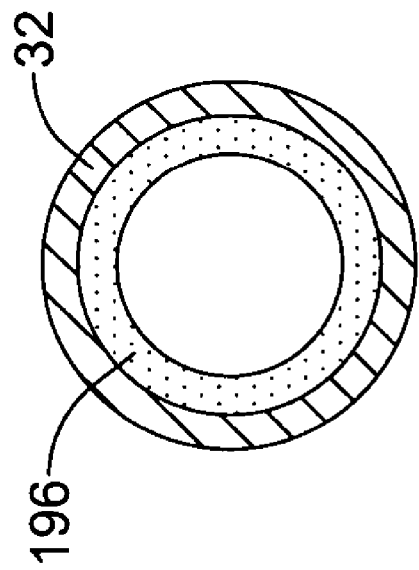
FIG. 18 is a cross-sectional view taken along line 18-18 of FIG. 16.
Figure 17:
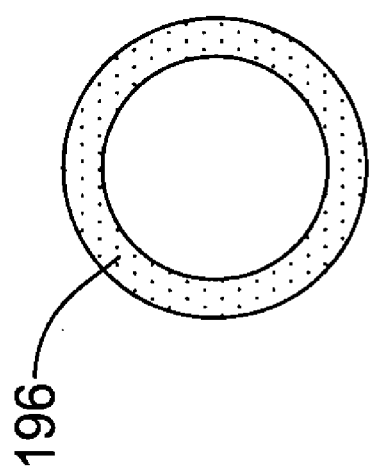
FIG. 17 is a cross-sectional view taken along line 17-17 of FIG. 16.

FIG. 16-18 illustrate another example use of the micromachined hypotubes discussed herein. FIG. 16 shows a catheter 186 having a proximal region 188 defining a proximal end 190 and a distal region 192 defining a distal end 194. As illustrated, catheter 186 is an over-the-wire, or single-operator-exchange (SOE) catheter, but is not limited to such. The catheter 186 includes a polymeric sheath 196 that extends from the proximal end 190 to the distal end 194. Micromachined hypotube 32 (FIG. 2) is seen deployed over polymeric sheath 196, as also illustrated in FIGS. 17 and 18.

The polymeric sheath 196 may be formed of any suitable polymeric material. Examples of suitable materials include polyethylene, polyurethane including high density polyurethane, elastomeric polyamides, block polyamide/ethers (such as PEBAX®), silicones, co-polymers, thermoplastic polymers such as a co-polyester thermoplastic elastomer such as that available commercially under the ARNITEL® name, and fluoropolymers such as PTFE.

In some instances, the polymeric sheath 196 may be formed of particular materials and to particular dimensions such that the polymeric sheath 196 is highly flexible but lacks sufficient column strength for pushing the catheter 186 through a body lumen. The micromachined hypotube 32 provides a desired level of column strength without excessively impacting flexibility.

In some instances, the distal end 38 of the micromachined hypotube 32 may be positioned proximal of the distal end 194 of the catheter 186 in order to not impact the flexibility of the distal end 194. In some cases, the distal end 38 of the micromachined 32 may be positioned at least about 4 centimeters from the distal end 194 and no more than about 20 centimeters from the distal end 194. If the distal end 38 of the micromachined hypotube 32 is too far from the distal end 194 of the catheter 186, pushability may suffer. Conversely, if the distal end 38 is too close to distal end 194, flexibility can suffer.

As illustrated, the proximal end 34 of the micromachined hypotube 32 ends at a position that is distal to the proximal end 190 of the catheter 186. In some instances, the micromachined hypotube 32 may extend further proximally such that the proximal end 34 is adjacent to or even proximal of the proximal end 190 of the catheter 186. It is contemplated that extending the micromachined hypotube 32 proximally of the proximal end 190 of the catheter 186 may provide handling advantages.

FIG. 19 illustrates a particular application of a micromachined hypotube as contemplated herein. In FIG. 19, a distal portion 200 of a catheter 198 is shown. The catheter 198 may be any particular intravascular catheter and can include one or more marker bands 202. Marker bands 202 are unique in that they are sections of micromachined hypotubes such as those discussed with respect to FIGS. 1 through 5. By using micromachined hypotubes as marker bands 202, additional flexibility may be achieved. Marker bands 202 may be formed of any suitably radiopaque material, such as gold, platinum, palladium, tantalum, tungsten alloy, and the like.

Figure 20:
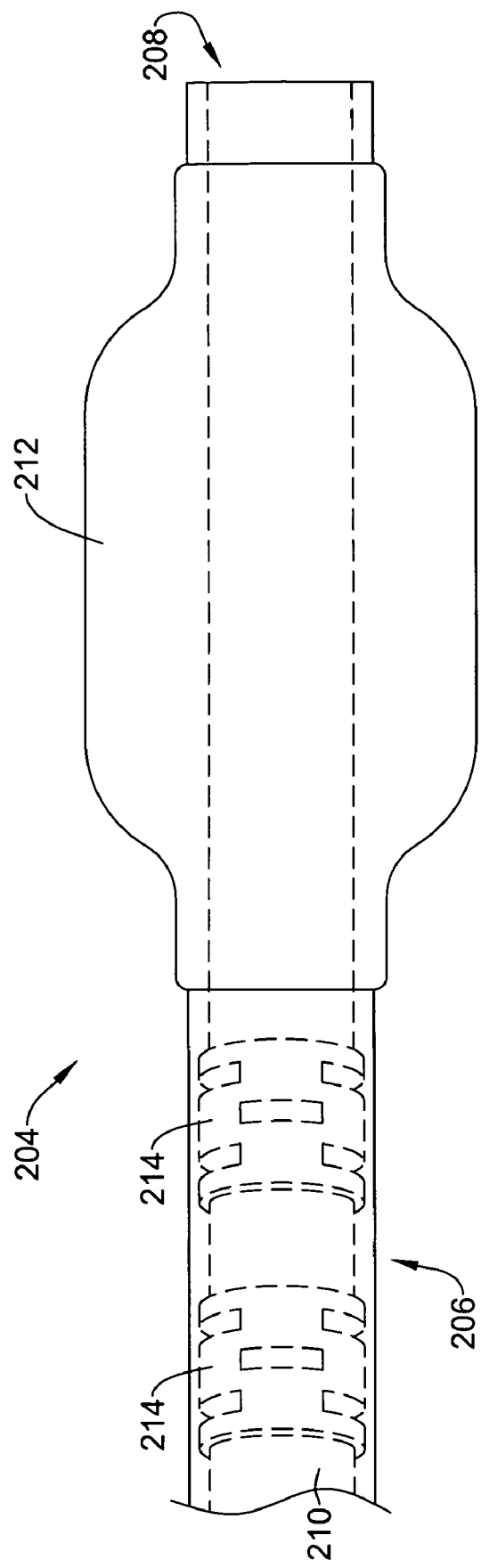
FIG. 20 is a view of a portion of a catheter in accordance with an embodiment of the invention.

FIG. 20 illustrates another particular application of a micromachined hypotube such as those discussed with respect to FIGS. 1 through 5. FIG. 20 is a partial longitudinal cross-section of a distal portion 206 of a balloon catheter 204 having a distal end 208. The balloon catheter 204 includes an elongate shaft 210 and a balloon 212 disposed on the elongate shaft. One or more compression rings 214 are positioned within the elongate shaft 210, proximal of the balloon 212. The compression rings 214 are unique in that they are sections of micromachined hypotubes such as those discussed with respect to FIGS. 1 through 5. By using micromachined hypotubes as compression rings 214, additional flexibility may be achieved.

In some instances, the elongate shaft 210 may have a very thin sidewall, which may be useful in terms of flexibility and profile. However, if the elongate shaft 210 has too thin of a sidewall, it can be in danger of collapsing in on itself when a vacuum is applied to the interior of the elongate shaft 210 in order to, for example, fully collapse the balloon 212. Thus, compression rings 214 can help prevent elongate shaft 210 from collapsing on itself.

Figure 21:
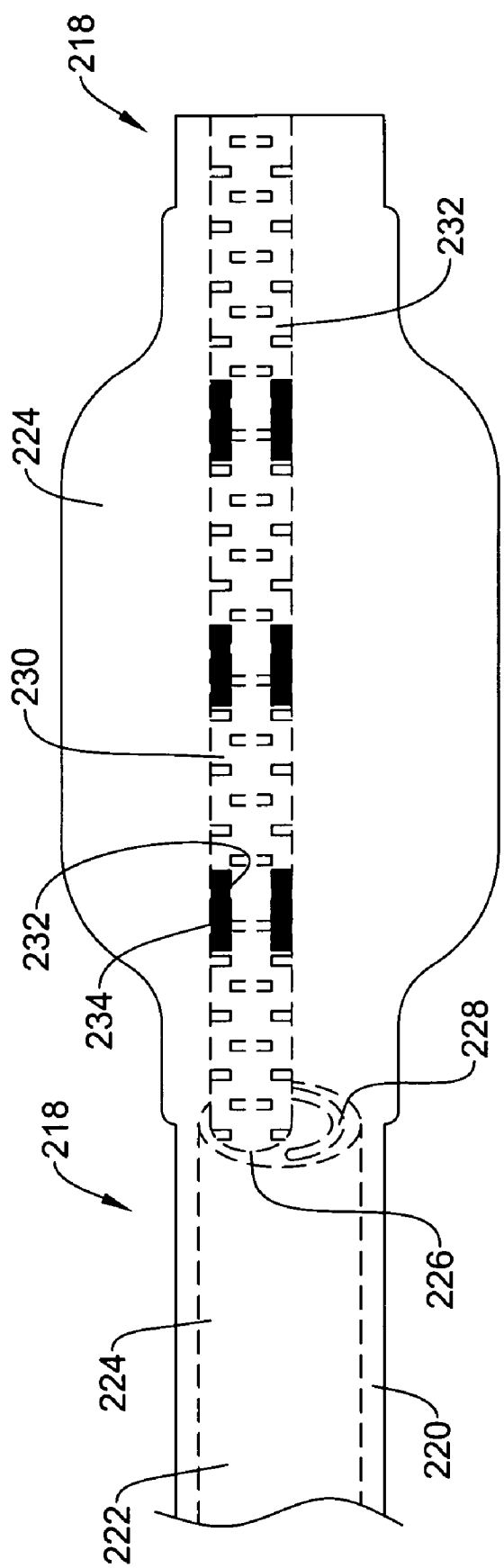
FIG. 21 is a view of a portion of a catheter in accordance with an embodiment of the invention.

FIG. 21 illustrates another use of a micromachined hypotube such as those discussed with respect to FIGS. 1 through 5. FIG. 21 is a partial longitudinal cross-section of a balloon catheter 216. The balloon catheter 216 has a distal end 218. The balloon catheter 216 includes an outer sheath 220 that extends to the distal end 218 and an inner assembly 222 including a portion that extends to the distal end 218 and a portion that does not. A balloon 224 is disposed on the outer sheath 220.

Inner assembly 222 includes a polymeric liner 224 defining a guidewire lumen 226 and an inflation lumen 228. A micromachined hypotube 230, similar to any of those discussed previously, extends distally from the guidewire lumen 226 and extends to the distal end 218 of the balloon catheter 216. The micromachined hypotube 230 includes at least one cut-out 232 configured to accommodate at least one marker band 234. The at least one marker band 234 can be of conventional construction. In some instances, the at least one marker band 234 may be a section of a micromachined hypotube, as shown in FIG. 19.

Figure 22:
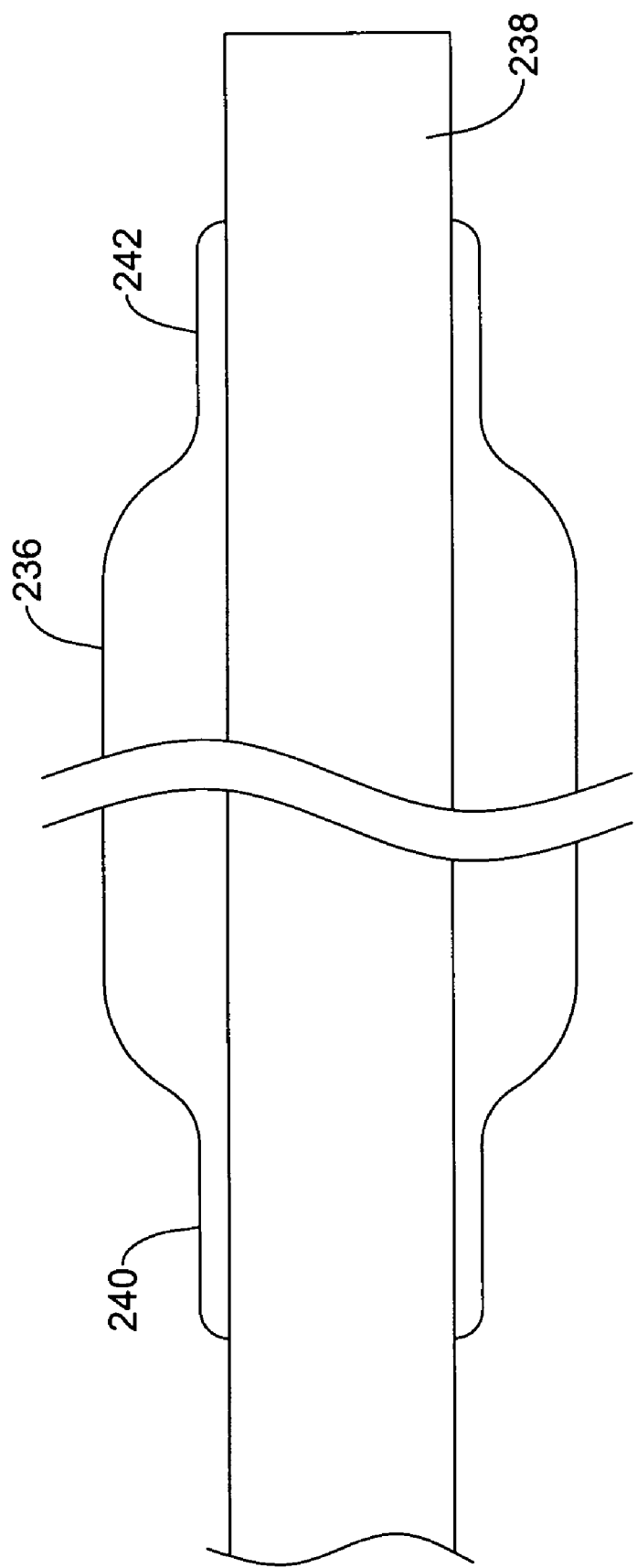
FIG. 22 is a view of a balloon bonded to a catheter shaft in accordance with an embodiment of the invention.
Figure 23:
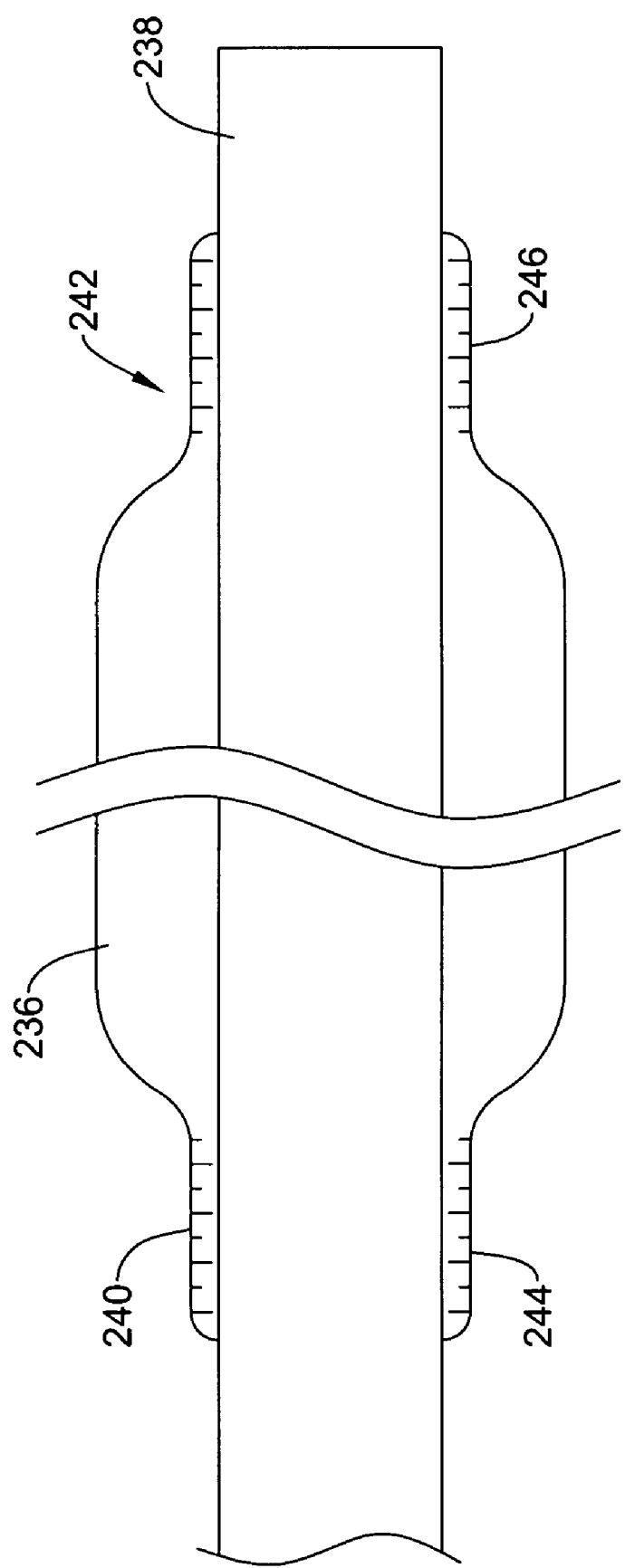
FIG. 23 is a view of the balloon of FIG. 22, illustrating post-attachment processing in accordance with an embodiment of the invention.

FIGS. 22-23 illustrate a particular embodiment in which micromachining techniques have been applied to a polymeric assembly. In particular, FIG. 22 illustrates a balloon 236 bonded to a shaft 238. The balloon 236 and the shaft 238 may be formed of any suitable material and may be constructed by any known process. The balloon 236 includes a proximal waist 240 and a distal waist 242. In some instances, the balloon 236 may be secured to the shaft 238 by bonding the proximal waist 240 and the distal waist 242 to the shaft 238.

While bonding the proximal waist 240 and the distal waist 242 to the shaft 238 provides an appropriate attachment method, there may be flexibility issues caused by the increased material thickness present at the proximal waist 240 and the distal waist 242. Thus, as illustrated in FIG. 23, a series of cuts 244 can be formed within the proximal waist 240 and a series of cuts 246 can be formed within the distal waist 242 in order to improve flexibility. The series of cuts 244 and the series of cuts 246 may be formed using any suitable technique. In some instances, these cuts 244 and 246 may be formed using the micromachining techniques used to form the micromachined hypotubes discussed with respect to FIGS. 1 through 5.

FIGS. 24 through 27 illustrate another contemplated use of the micromachined hypotubes discussed herein. In some instances, there may be a desire to have an outer shaft at least somewhat free to move with respect to an inner shaft, yet be able to lock the outer shaft with respect to the inner shaft when necessary.

Figure 24:
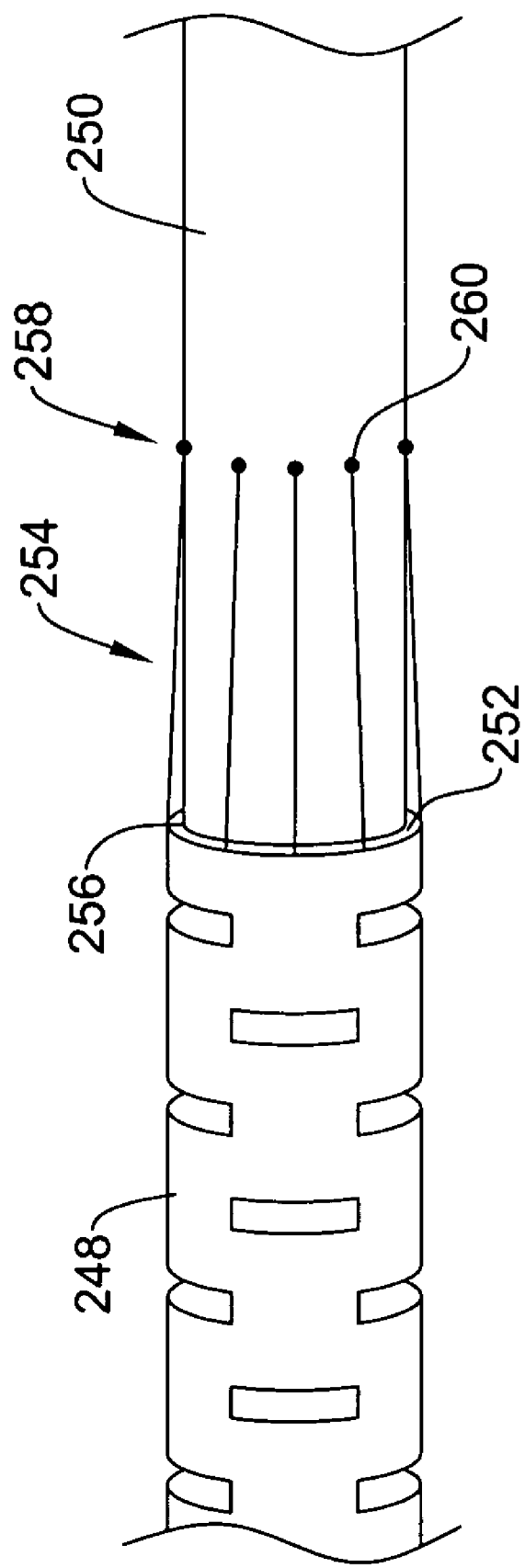
FIG. 24 is a view of an assembly including outer shaft attached to an inner shaft via a collapsible cage in accordance with an embodiment of the invention.

FIG. 24 shows an outer shaft 248 deployed over an inner shaft 250. The outer shaft 248 has a distal end 252. As illustrated, the outer shaft 248 may be a micromachined hypotube while the inner shaft 250 may be a catheter shaft or a guidewire. In some instances, both the outer shaft 248 and the inner shaft 250 may be micromachined hypotubes such as those discussed herein.

A collapsible cage 254 having a proximal end 256 and a distal end 258 is deployed over the inner shaft 250 proximate the distal end 252 of the outer shaft 248. The proximal end 256 of the collapsible cage 254 can be secured to the distal end 252 of the outer shaft 248 while the distal end 258 of the collapsible cage 254 can be secured to an attachment point 260 (or a number of attachment points 260) present on the inner shaft 250. In some instances, the collapsible cage 254 may be welded or soldered to the outer shaft 248 and the inner shaft 250, respectively.

The collapsible cage 254 may be formed of a number of wires 262 formed of any suitable material such as stainless steel or nitinol. Similarly, the outer shaft 248 and the inner shaft 250 may also be formed of stainless steel or nitinol.

Figure 25:
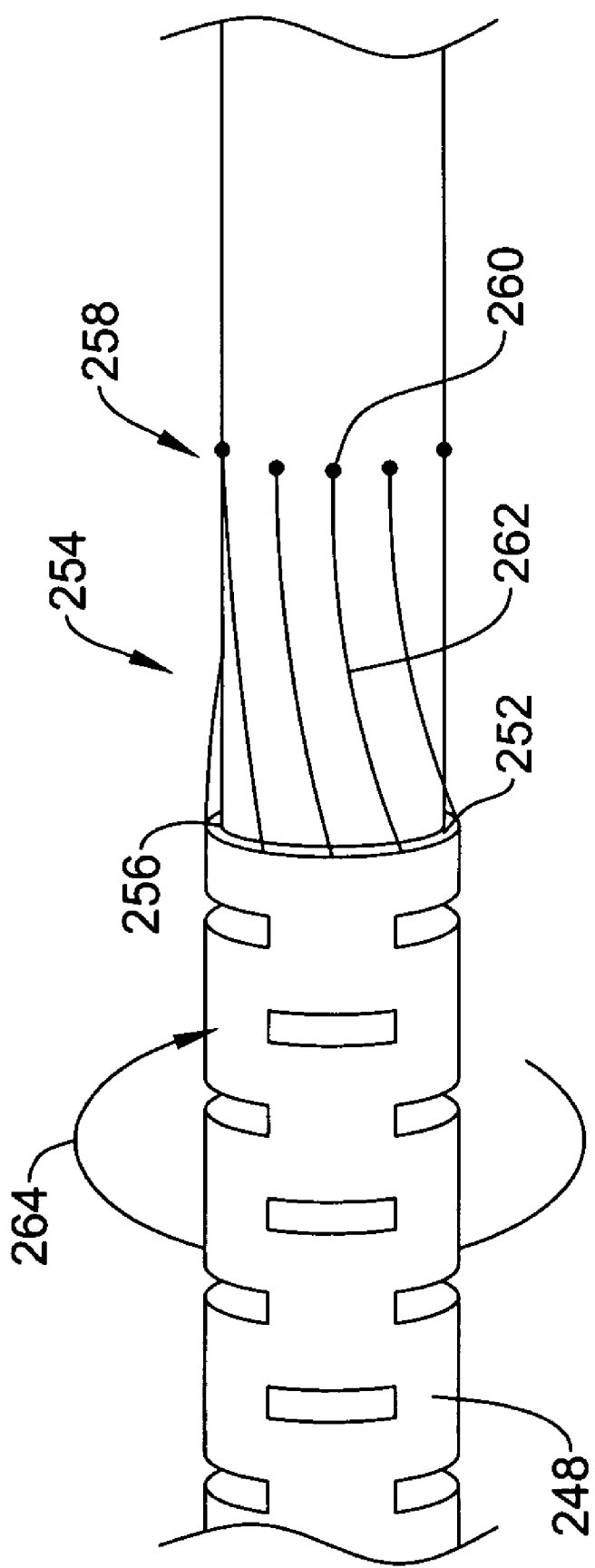
FIG. 25 is a view of the assembly of FIG. 24, shown with the cage in a collapsed configuration in accordance with an embodiment of the invention.

As illustrated, the outer shaft 248 has an inner diameter that is somewhat greater than an outer diameter of the inner shaft 250 and thus the outer shaft 248 enjoys some limited relative movement with respect to the inner shaft 250. FIG. 25 illustrates how the outer shaft 248 may be locked into position relative to the inner shaft 250.

In FIG. 25, the outer shaft 248 has been rotated with respect to the inner shaft 250 as indicated by rotation arrow 264. As the outer shaft 248 rotates with respect to the inner shaft 250, the collapsible cage 254 tightens as individual wires 262 twist. Once the outer shaft 248 rotates a given angular distance, any additional rotation in the same direction will cause the inner shaft 250 to rotate with the outer shaft 248.

Figure 26:
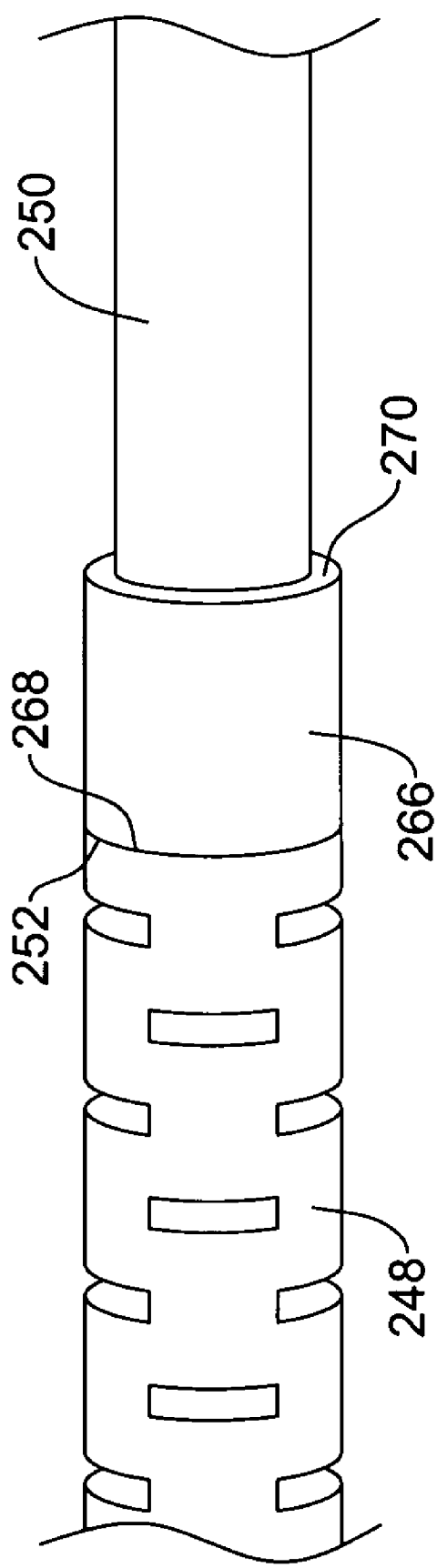
FIG. 26 is a view of an assembly including an outer shaft attached to an inner shaft via a collapsible electroactive polymer sleeve in accordance with an embodiment of the invention.
Figure 27:
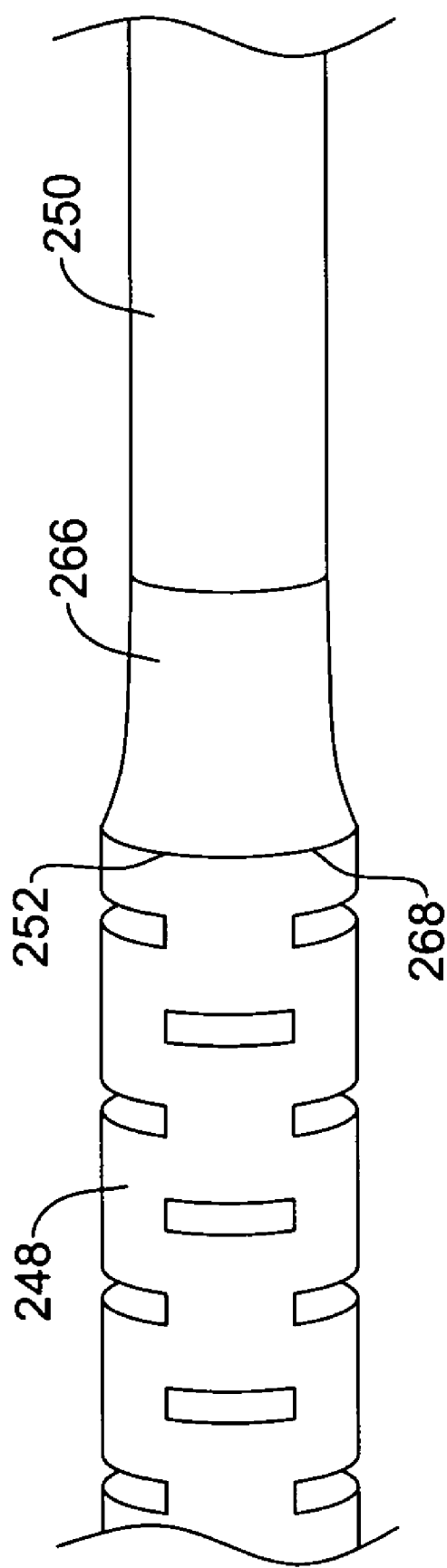
FIG. 27 is a view of the assembly of FIG. 26, shown with the electroactive polymer sleeve in a collapsed configuration in accordance with an embodiment of the invention.

FIGS. 26-27 illustrate a similar principle, but utilize a different locking mechanism. In FIG. 26, collapsible cage 254 has been replaced with a polymer sleeve 266, which has a proximal end 268 and a distal end 270. The polymer sleeve 266 can be formed of an electro-active polymer. The proximal end 268 is secured to the distal end 252 of the outer shaft 248 while the distal end 270 is secured to an attachment point 260 positioned on the inner shaft 250.

As illustrated, the outer shaft 248 has an inner diameter that is somewhat greater than an outer diameter of the inner shaft 250 and thus the outer shaft 248 enjoys some limited relative movement with respect to the inner shaft 250. The inner shaft 250 may rotate somewhat with respect to the outer shaft 248, or may in some cases translate distally or proximally with respect to the outer shaft 248. FIG. 27 illustrates how the outer shaft 248 may be locked into position relative to the inner shaft 250.

In FIG. 27, an electrical current has been applied to the polymer sleeve 266, thereby causing the polymer sleeve 266 to contract down onto the inner sleeve 250 and thus prevent relative rotational movement between the inner shaft 248 and the outer shaft 250. In some instances, a current may be transmitted to the polymer sleeve 266 via the outer shaft 248.

Figure 28:
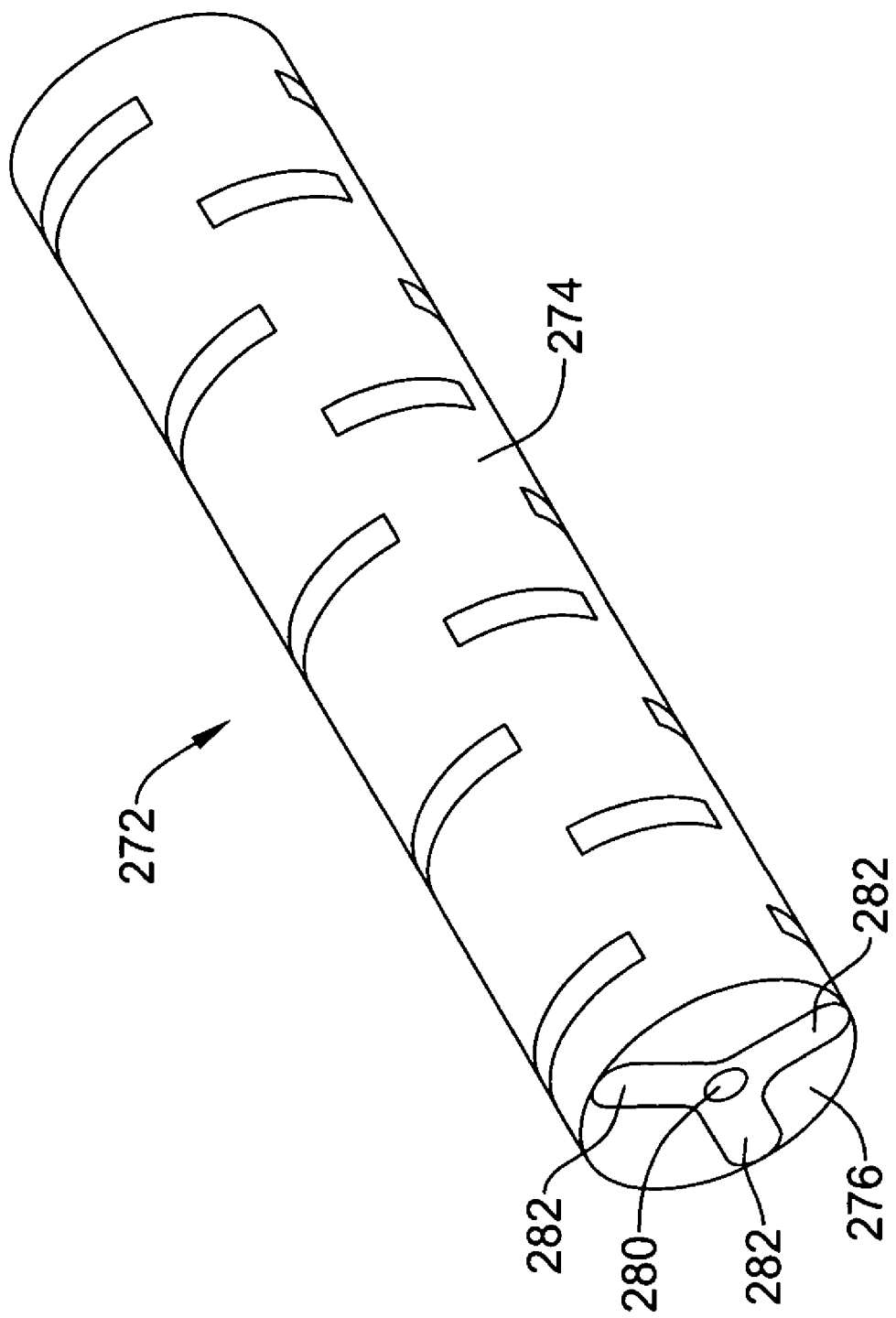
FIG. 28 is a view of an assembly in accordance with an embodiment of the invention.
Figure 29:
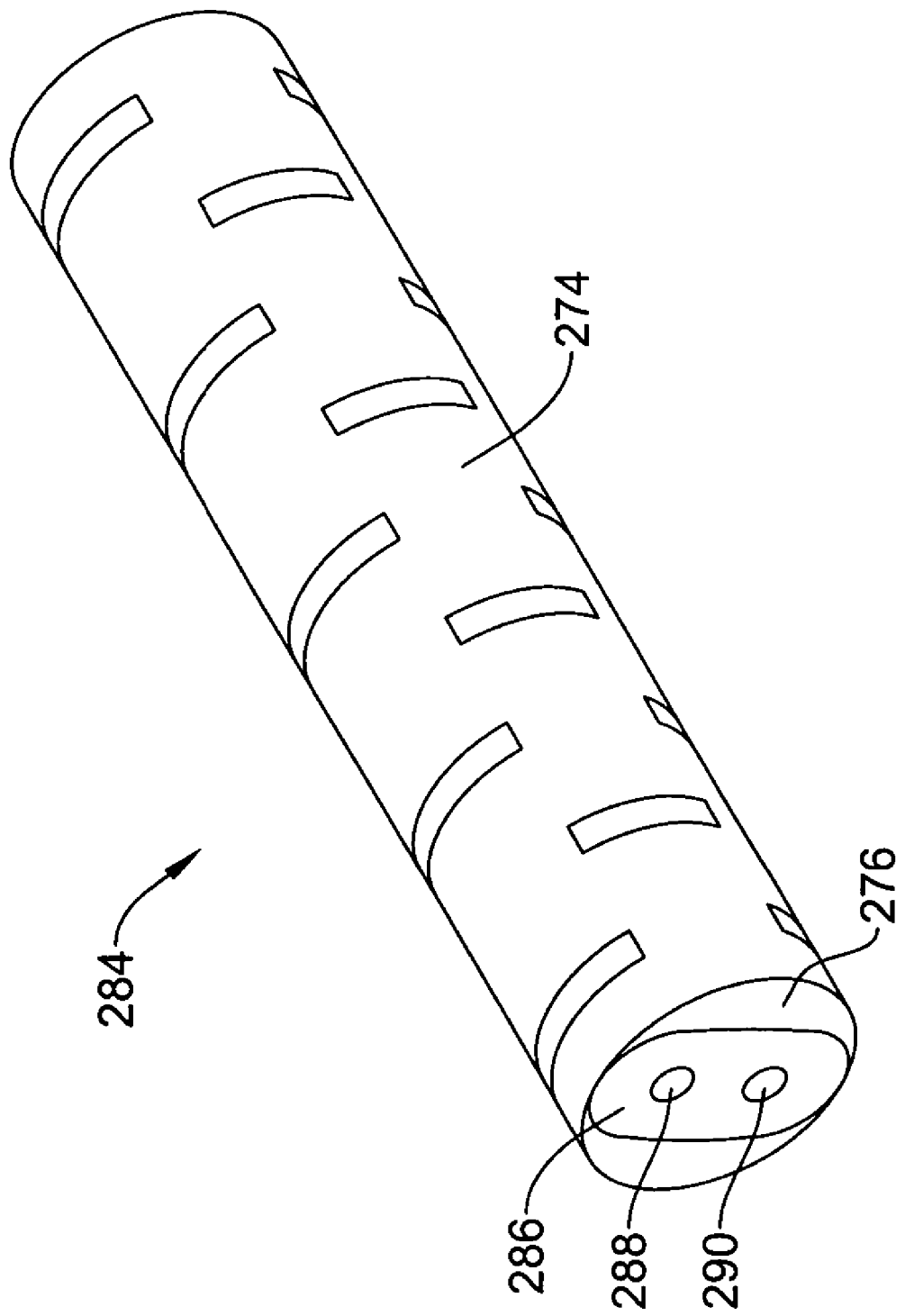
FIG. 29 is a view of an assembly in accordance with an embodiment of the invention.
Figure 30:
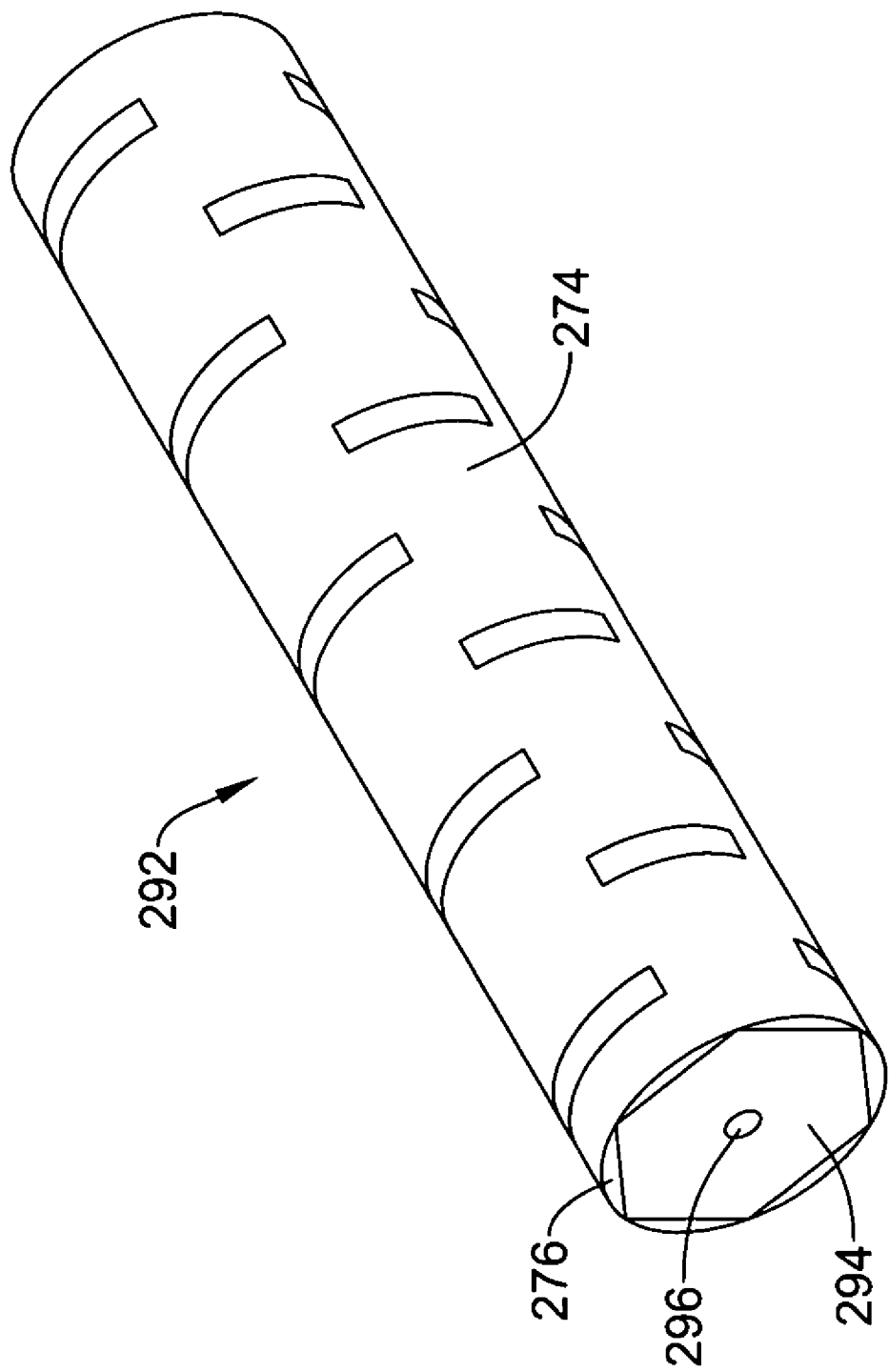
FIG. 30 is a view of an assembly in accordance with an embodiment of the invention.

FIGS. 28-30 illustrate additional uses for the micromachined hypotubes described herein. FIG. 28 shows an assembly 272 that may be used, for example, as a catheter. The assembly 272 includes a micromachined hypotube 274 having an interior 276. A polymeric liner 278 is disposed within the interior 276. In the illustrated embodiment, the polymeric liner 278 defines a lumen 280 and includes three lobes 282. In some instances, the three lobes 282 are configured to center the polymeric liner 278 and thus the lumen 280 within the interior 276. In other embodiments, the polymeric liner 278 may include four or more lobes 282.

FIG. 29 shows an assembly 284 that can be used as a catheter. The assembly includes a micromachined hypotube 274 having an interior 276. A polymeric liner 286 is disposed within the interior 276. The polymeric liner 286 defines a first lumen 288 and a second lumen 290, and has an ovoid cross-sectional shape. The ovoid cross-sectional shape may, in some instances, help to center the polymeric liner 286 within the interior 276.

FIG. 30 shows an assembly 292 that can be used as a catheter. The assembly includes a micromachined hypotube 274 having an interior 276. A polymeric liner 294 is disposed within the interior 276. The polymeric liner 294 defines a lumen 296 and has a polygonal cross-sectional shape. The polygonal cross-sectional shape may, in some instances, help to center the polymeric liner 294 within the interior 276. In the illustrated embodiment, the polymeric liner 294 has a six-sided cross-section. In some instances, the polymeric liner 294 may have a four-sided, a five-sided, a seven-sided or even an eight-sided cross-section.

Figure 31:
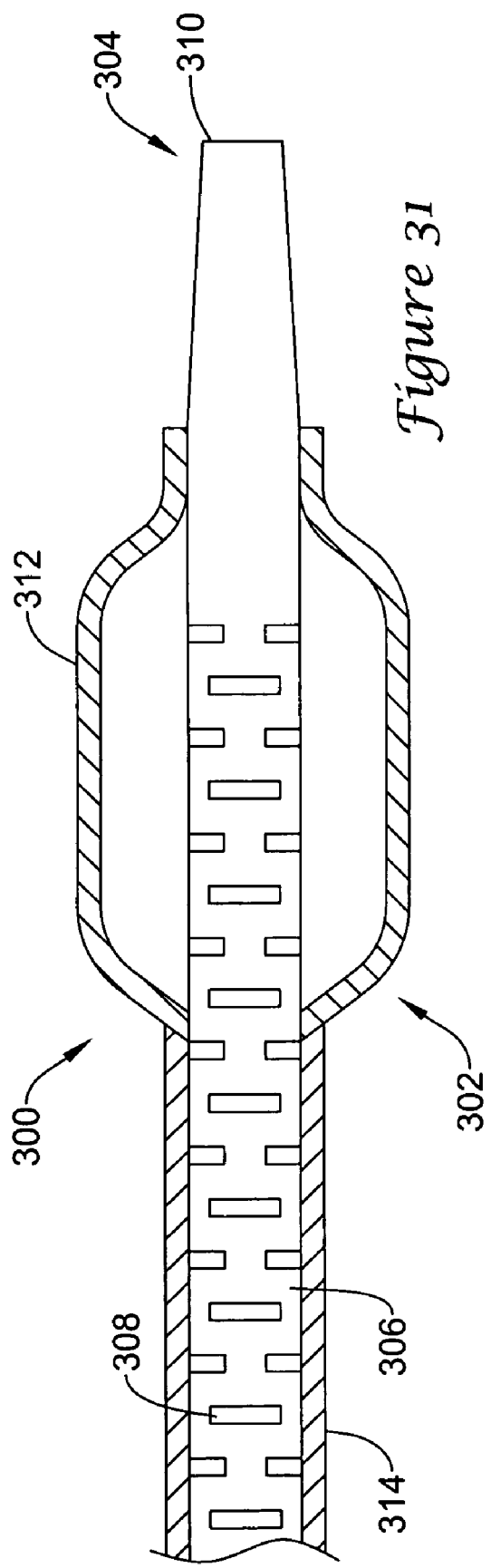
FIG. 31 is a view of a portion of a catheter in accordance with an embodiment of the invention.
Figure 32:
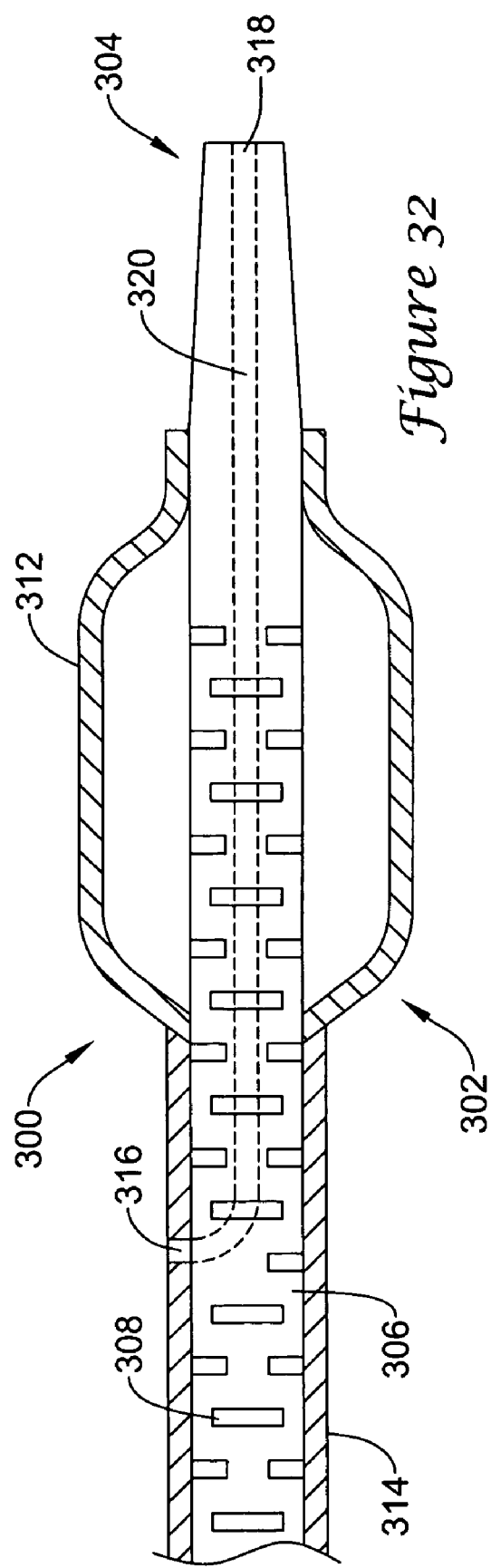
FIG. 32 is a view of a portion of a catheter in accordance with an embodiment of the invention.

FIGS. 31 and 32 show another particular application of a micromachined hypotube such as those discussed herein with respect to FIGS. 1 through 5. FIGS. 31 and 32 show a portion of a catheter 300 having a distal region 302 defining a distal end 304. The catheter 300 includes a micromachined hypotube 306 that may be constructed as discussed with respect to the micromachined hypotubes shown in FIGS. 1 through 5. The micromachined hypotube 306 may include a number of slots 308. In some instances, all of the micromachined hypotube 306 may include slots 308 while in other cases only distinct portions may include slots 308, depending on the flexibility requirements.

A hypotube lumen 310 extends through the micromachined hypotube 306 to the distal end 304 thereof. An inflatable balloon 312 is disposed about the distal region 302 of the catheter 300. An outer sheath 314 may be disposed proximal of the inflatable balloon 312 and may cover at least a portion of the distal region 302 not covered by the inflatable balloon 312. As a result, the hypotube lumen 310 may be used to inflate and deflate the inflatable balloon 312. The inflatable balloon 312 and the outer sheath 314 may be formed of any suitable polymeric material, such as those discussed previously. As shown, the outer sheath 314 abuts the inflatable balloon 312, but it is contemplated that the outer sheath 314 may overlap a portion of the inflatable balloon 312, or, in the alternative, a portion of the inflatable balloon 312 may overlap a portion of the outer sheath 314.

In some instances, the hypotube lumen 310 may be sized to accommodate a guidewire (not shown). In a fixed wire configuration, it is contemplated that a distal portion of the hypotube lumen 310 include a plug or other structure to seal the interior of the hypotube lumen 310. In an over-the-wire configuration, it is contemplated that the hypotube lumen 310 may include sealing structure (not shown) adapted to permit a guidewire to pass through the sealing structure yet be at least substantially fluid tight against the guidewire.

In some instances, as shown for example in FIG. 32, the catheter 300 may be configured for rapid exchange. In this embodiment, the catheter 300 includes a proximal guidewire port 316, a distal guidewire port 318 and a guidewire lumen 320 that extends from the proximal guidewire port 316 to the distal guidewire port 318. The guidewire lumen 320 is seen in phantom in FIG. 32.

In some embodiments, part or all of the devices described herein can include a lubricious coating. Lubricious coatings can improve steerability and improve lesion crossing capability. Examples of suitable lubricious polymers include hydrophilic polymers such as polyarylene oxides, polyvinylpyrolidones, polyvinylalcohols, hydroxy alkyl cellulosics, algins, saccharides, caprolactones, and the like, and mixtures and combinations thereof. Hydrophilic polymers can be blended among themselves or with formulated amounts of water insoluble compounds (including some polymers) to yield coatings with suitable lubricity, bonding, and solubility. In some embodiments, portions of the devices described herein can be coated with a hydrophilic polymer or a fluoropolymer such as polytetrafluoroethylene (PTFE), better known as TEFLON®.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

We claim:

1. A catheter having a distal region and a proximal region, the catheter comprising:
    an elongate tube having a distal end and a proximal end defining a length therebetween, the elongate tube extending from the proximal region to a distal end of the distal region, the elongate tube comprising a plurality of slots disposed substantially along the entire length of the elongate tube, the slots extending radially about the elongate tube, each slot extending only partially around the circumference of the elongate tube, at least two of the slots being disposed at the same axial position along the elongate tube; and
    a polymeric dual-lumen liner disposed within the elongate tube.

2. The catheter of claim 1, wherein the elongate tube comprises an elongate metal tube.

3. The catheter of claim 1, further comprising a hub disposed at the proximal end of the elongate tube and at least one aperture, distinct from the slots, disposed near where the hub meets the proximal end of the elongate tube, the at least one aperture adapted to accommodate additional polymeric material to secure the polymeric dual-lumen liner to the elongate tube.

4. The catheter of claim 1, further comprising a proximal guidewire port disposed between the distal region of the catheter and the proximal region of the catheter.

5. The catheter of claim 4, wherein the elongate tube comprises at least one aperture, distinct from the slots, disposed near where the proximal guidewire port, the at least one aperture adapted to accommodate additional polymeric material to secure the polymeric dual-lumen liner to the elongate tube.

6. The catheter of claim 4, wherein the elongate tube further comprises a guidewire aperture aligned with the proximal guidewire port.

7. The catheter of claim 1, further comprising a balloon secured to the distal region of the catheter.

8. The catheter of claim 7, wherein the elongate tube comprises at least one aperture, distinct from the slots, disposed near where the balloon is secured to the elongate tube, the at least one aperture adapted to accommodate additional polymeric material to secure the polymeric dual-lumen liner to the elongate tube.

9. The catheter of claim 1, wherein the polymeric dual-lumen liner comprises a round guidewire lumen and a crescent-shaped inflation lumen.

10. The catheter of claim 1, wherein the polymeric dual-lumen liner comprises high density polyethylene.

11. A catheter having a distal region and a proximal region, the catheter comprising:
    an elongate metal tube having a length extending from the proximal region to a distal end of the distal region, the elongate metal tube comprising a plurality of slots disposed substantially along the entire length of the elongate metal tube, the slots extending radially about the elongate metal tube, each slot extending only partially around the circumference of the elongate metal tube, at least two of the slots being disposed at the same axial position along the elongate metal tube;
    a polymeric sleeve disposed about the elongate metal tube; and
    a polymeric dual-lumen liner disposed within the elongate metal tube.

12. The catheter of claim 11, wherein the polymeric dual-lumen liner comprises a round guidewire lumen and a crescent-shaped inflation lumen.

13. The catheter of claim 12, further comprising a proximal guidewire port disposed between the distal region of the catheter and the proximal region of the catheter, the proximal guidewire port providing access to the guidewire lumen.

14. The catheter of claim 13, wherein the elongate metal tube has a proximal portion proximal to the proximal guidewire port and a distal portion distal to the proximal guidewire port, the proximal portion having a round cross-section and the distal portion having a semi-circular cross-section.

15. The catheter of claim 14, wherein the distal portion of the elongate metal tube obtains a semi-circular cross-section by removal of a portion of the elongate metal tube.

16. The catheter of claim 14, wherein the distal portion of the elongate metal tube obtains a semi-circular cross-section by crushing a portion of the elongate metal tube.

\* \* \* \* \*